United States Patent [19]

Walsh et al.

[11] Patent Number: 5,248,606
[45] Date of Patent: Sep. 28, 1993

[54] DNA ENCODING INACTIVE PRECURSOR AND ACTIVE FORMS OF MAIZE RIBOSOME INACTIVATING PROTEIN

[75] Inventors: Terence A. Walsh; Timothy D. Hey; Alice E. R. Morgan, all of Midland, Mich.

[73] Assignee: DowElanco, Indianapolis, Ind.

[21] Appl. No.: 535,636

[22] Filed: Jun. 11, 1990

[51] Int. Cl.⁵ .................. C12N 5/10; C12N 15/29; C12N 15/63; C12N 1/21
[52] U.S. Cl. .................. 435/240.4; 536/23.6; 435/320.1; 435/240.2; 435/252.3; 435/254.21; 530/376; 935/10; 935/11; 935/67
[58] Field of Search .................. 536/27, 23.6; 435/320.1, 252.3, 240.2, 240.4, 255; 934/9, 11, 60, 67, 10; 530/376

[56] References Cited

U.S. PATENT DOCUMENTS 4,869,903  9/1989  Lifson et al. .................. 424/195.1

FOREIGN PATENT DOCUMENTS 7556487  1/1988  Australia .
390040  10/1990  European Pat. Off. .
402544  12/1990  European Pat. Off. .
8703286  6/1987  PCT Int'l Appl. .
2194241  7/1987  United Kingdom .
2216891  1/1989  United Kingdom .

OTHER PUBLICATIONS

Boswell, D. et al. 1988, In: *Computational Molecular Bioilogy, Sources and Methods for Sequence Analysis*, ed. A. M. Lesk, Oxford University Press, pp. 161-178.
Schwall, M. et al. 1988, *Biological Abstracts*, vol. 86, No. 7, p. AB-489-490, Abstract 69622.
Hartings et al., (1990), *Plant Molecular Biology*, 14:1031-1040.
Lohmer et al., (1991), the *EMBO Journal*, 10(3):617-62.
DiFonzo et al., (1986), *Planta*, 167:587-594.
DiFonzo et al., (1988), *Mol. Gen. Genet.*, 212:481-487.

*Primary Examiner*—David T. Fox
*Assistant Examiner*—Mary E. Mosher
*Attorney, Agent, or Firm*—Thomas D. Zwdrick; Kenneth L. Loertscher

[57] ABSTRACT

The present invention is directed to a ribosome inactivating protein from maize. The protein is characterized by being in a single chain proRIP inactive form that can be converted into an active form by cleavage with proteases.

10 Claims, 18 Drawing Sheets

FIG. 1

```
  1      GAA TTC GGC ACG AGC AAA GAG AAG GGA ATG GCC GAG ATA ACC CTA GAG CCG
  1      Glu Phe Gly Thr Ser Lys Glu Lys Gly Met Ala Glu Ile Thr Leu Glu Pro

52      AGT GAT CTT ATG GCG CAA ACA AAC AAA AGA ATA ATA CCA AAG TTC ACT GAA
  9      Ser Asp Leu Met Ala Gln Thr Asn Lys Arg Ile Ile Pro Lys Phe Thr Glu

103      ATC TTC CCC GTG GAG GAC GCG TAC CCT TAC AGC GCC TTC ATC GCG TCG
 26      Ile Phe Pro Val Glu Asp Ala Tyr Pro Tyr Ser Ala Phe Ile Ala Ser

154      GTC CGG AAA GAC GTG ATC AAA CAC TGC ACC GAC CAT AAA GGG ATC TTC CAG
 43      Val Arg Lys Asp Val Ile Lys His Cys Thr Asp His Lys Gly Ile Phe Gln

205      CCC GTG CTG CCA CCG CCG GAG AAG GTC CCG GAG CTA TTC TAC ACA GAG
 60      Pro Val Leu Pro Pro Pro Glu Lys Val Pro Glu Leu Trp Phe Tyr Thr Glu

256      CTC AAA ACT AGG ACC AGC ATC TCC ACG CTC GCC ATA CGC ATG GAC AAC CTG
 77      Leu Lys Thr Arg Thr Ser Ile Ser Thr Leu Ala Ile Arg Met Asp Asn Leu

307      TAC CTC GTG GGC TTC AGG ACC CCG GGG GTG TGG TGG GAG TTC GGC AAG
 94      Tyr Leu Val Gly Phe Arg Thr Pro Gly Val Trp Trp Glu Phe Gly Lys
```

FIG. 1 (CONT.)

```
358  GAC GGC GAC ACC CAC CTC CTC GGC GAC AAC CCC AGG TGG CTC GGC TTC GGC
111  Asp Gly Asp Thr His Leu Leu Gly Asp Asn Pro Arg Trp Leu Gly Phe Gly

409  GGC AGG TAC CAG GAC CTC ATC GGC AAC AAG GGT CTG GAG ACC GTC ACC ATG
128  Gly Arg Tyr Gln Asp Leu Ile Gly Asn Lys Gly Leu Glu Thr Val Thr Met

460  GGC CGC GAA ATG ACC AGG GCC AAC GTC AAC GAC CTG AAG GCG AAG AAG AAG
145  Gly Arg Glu Met Thr Arg Ala Asn Val Asn Asp Leu Lys Ala Lys Lys Lys

511  ATG GCG ACA CTG GAG GAG GAG GTG AAG ATG CAG ATG CAG CCG GAG
162  Met Ala Thr Leu Glu Glu Glu Val Lys Met Gln Met Gln Pro Glu

562  GCC GCT GAT CTG GCG GCA GCG GCT GAC CCA CAG GCC GAC ACG AAG
179  Ala Ala Asp Leu Ala Ala Ala Ala Asp Pro Gln Ala Asp Thr Lys

613  AGC AAG CTG GTG GTC ATG GTG TGC GAG GGG CTG CGG TTC AAC
196  Ser Lys Leu Val Val Met Val Cys Glu Gly Leu Arg Phe Asn

664  ACC GTG TCC CGC ACG GTG GAC GCG GGG TTC AAC AGC CAG CAC GGG GTG ACC
213  Thr Val Ser Arg Thr Val Asp Ala Gly Phe Asn Ser Gln His Gly Val Thr
```

FIG. 1 (CONT.)

```
715  TTG ACC GTG ACG CAG GGG AAG CAG GTG CAG AAG TGG GAC AGG ATC TCC AAG
230  Leu Thr Val Thr Gln Gly Lys Gln Val Gln Lys Trp Asp Arg Ile Ser Lys

766  GCC GCC TTC GAG TGG GCT GAC CAC CCC ACC GCT GTG ATC CCC GAC ATG CAG
247  Ala Ala Phe Glu Trp Ala Asp His Pro Thr Ala Val Ile Pro Asp Met Gln

817  AAG CTT GGC ATC AAG GAT AAG AAC GCA AGG ATC GCG AGG ATC GCG CTC GTT
264  Lys Leu Gly Ile Lys Asp Lys Asn Ala Arg Ile Ala Arg Ile Ala Leu Val

868  AAG AAT CAA ACT ACT GCT GCC GCT ACT GCC AGT GCT GAC AAC GAC
281  Lys Asn Gln Thr Thr Ala Ala Ala Thr Ala Ser Ala Asp Asn Asp

919  GAC GAC GAG GCC TGA TCA ATG CAA CGA CAC ATC ATG ATC TGC TGC ACT
298  Asp Asp Glu Ala End

970  TAA TTA CTA CTA TGT CGT TAT ACA AAT AAA TAC ACC CGG CGT ACG CGG TGT TCC

1021 TTA TAT GGT CTA AAA TGT AGC CAG TAA ATT TTA AAC TAC TTT CTC GTG CCG

1072 AAT TC
```

FIG. 3

```
1    MAEITLEPSDLMAQTNKRIVPKFTEIFPVEDANYPYSAFIASVRKDVIKHCTDHKGIFQPV
1    ------------AAKMAKNVDKPLFTATFNVQASSADYATFIAGIRNKLRNPA---HFSHNEPV

61   LPP-EKKVPEL-WFYTELKTR-TSS-ITLAIRMDNLYLVGFRTPGGVWWEFGKDGDTHLLG
50   LPPVEPNVPPSRWFHVVLKASPTSAGLTLAIRADNIYLEGFKSSDGTWWELTPGLIPGAT-

119  DNPRWLGFGGGRYQDLIGNKGLET--VTMGRAEMTRAVNDLAKKKKMATLEEEEVKMQMQMPE
110  ----YVGFGGTYRDLLGDTDKLTNVALGRQQLEDAVTALHGRTK----------------

187  AADLAAAAADPQADTKSKLVKLVVMVCEGLRFNTVSRTVDAGFNSQHGVTLT----VTQG
150  ----ADKASGPKQQQAREAVTTLLLMVNEATRFQTVSGFVAGLLHPKAVEKKSGKIGNEMK

236  KQVQKWDRISKAAFEWADHPTAVIPDMQKLGIKDKNEAARIVALVKNQTTAAAATAASADN
207  AQVNGWQDLS-AALLK----TDVKPPPGKSPAKFTPIEKMGVRTAEQ----AAATLGILLF

297  DDDEA
259  VEVPGGLTVAKALELFHASGGK
```

FIG. 4

```
  1  ------MAEITLEPSDLMAQTNKRIVPKFTEIFPVEDANYPYSAFIASVRKDVIKHCT
          ::                                    ::
-24  MYAVATWLCFGSTSGWSFTLEDNNIFPKQYPIINFTTAGATVQSYTNFIRAVRGRLTTGAD

62  DHKGIFQPVLPP-EKKVPELWF-YTELKTR-TSSITLAIRMDNLYLVGFRTPGGVWWEFGK
                                      ::  : ::  :         ::
 38  VR--HEIPVLPNRVGLPINQRFILVELSNHAELSVTLALDVTNAYVVVGYRAGNSAYFFHPD

110  DGDTHLLGDNPR------WLGFGGRYQDLIGNKGL--ETVTMGRAEMTRAVNDLAKKKM
        ::                                   ::
 97  NQEDAEAITHLFTDVQNRYTFAFGGNYDRLEQLAGNLRENIELGNPLEEAISALYYYST-

164  ATLEEEVKMQMQMPEAADLAAAAADPQADTKSKLVKLVVMVCEGLRFNTVSRTVDAGFN
                                          ::   ::     :: ::
157  -----------GGTQLPTLARSFIICIQMISEAARFQYIEGEMRTRIR

224  SQHGVTLTVTQGKQVQKWDRISKAAFEWADHPTAVIPDMQKLGI-KDKNEAARIVALVKNQ
        ::                              ::                ::
194  YNRRSAPDPSVITLENSWGRLSTAIQESNQGAFASPIQLQRRNGSKFSVYDVSILIPIIAL

284  TTAAAATAAASADNDDDEA
         —
  2  MVYRCAPPPSQF
```

FIG. 5A

```
                                  —            —|:   :|—      :
Maize RIP      AQTNKRIVPKFTEIF-PVEDANYPYSAFIASVRKDVIK
Barley RIP     AAKMAKNVDKPLFTATF-NVQASSADYATFIAGIRNKLRN
Ricin A        IFPKQYPIINFTTAGATVQSYTNFIRAVRGRLTT
Trichosanthin            DVSFRLSGATSSSYGVFISNLRKALPN
Momordin                 DVSFRLSGADPRSYGMFIKDLRNALPF
Bryodin                  DVSFRLSGATTTSYGVFIKNLREALPY
Gelonin            GLDTVSFSTKGATYITYVNFLNELRVKLKP
Dodecandrin        VNTIIYNVGSTTISNYATFMDNLRNEAKD
Pokeweed AP2     N-IVFDYENATPETYSNFLTSLREAVKD
Saporin 5          VTSITLDLVNPTAGQYSSFVDKIRNNVKD
Saporin 4          VIIYELNLQGTTKAQYSTILKQLRDDIKD
SLT-1A              KEFTLDFSTAKTYDSLNV-IRSAIGT
```

| | | | | | |
|---|---|---|---|---|---|
| Maize RIP | 84 | ITLAIRMDNLYLVGF | 201 | LVVMVCEGLRFNTVS | 237 QVQK-WDRISKA |
| Barley RIP | 77 | LTLAIRADNIYLEGF | 168 | LLLMVNEATRFQTVS | 208 QVNG-WQDLSAA |
| Ricin A-chain | 70 | VTLALDVTNAYVVGY | 171 | CIQMISEAARFQYIE | 207 LENS-WGRLSTA |
| Saporin-6 | 62 | VSLGLKRDNLYVVAY | 170 | AIQMTAEAARFRYIQ | 205 EVN--WKKISTA |
| Abrin A-chain | 64 | IEVGIDVTNAYVVAY | 159 | IIQVASEAARFRYIS | 194 LENN-WDNLRGV |
| SLT-1A | 62 | MIDSGSGDNLFAVDV | 183 | FVTVTAEALRFQIQR | 222 TLN--WGRLSSV |
| Trichosanthin | 58 | DEVALDVTNV.... | 161 | LIQSTSEAARYKFIE | 196 LENSLWLALSKQ |
| | 77 | YLMGY | | | |

```
  1  GCTTAATTAA TTAAGCTTAA AAGGAGGAAA AAAATTATGG CCGAGATAAC CCTAGAGCCG
 61  AGTGATCTTA TGGCGCAAAC AAACAAAAGA ATAGTGCCAA AGTTCACTGA AATCTTCCCC
121  GTGGAGGACG CGAACTACCC TTACAGCGCC TTCATCGCGT CGGTCCGGAA AGACGTGATC
181  AAACACTGCA CCGACCATAA AGGGATCTTC CAGCCCGTGC TGCCACCGGA GAAGAAGTC
241  CCGGAGCTAT GGTTCTACAC AGAGCTCAAA ACTAGGACCA GCTCCATCAC GCTCGCCATA
301  CGCATGGACA ACCTGTACCT CGTGGGCTTC AGGACCCCGG GCGGGGTGTG GTGGGAGTTC
361  GGCAAGGACG GCGACACCCA CCTCCTCGGC GACAACCCCA GGTGGCTCGG CTTCGGGGGC
421  AGGTACCAGG ACCTCATCGG CAACAAGGGT CTGGAGACCG TCACCATGGG CCGCGCCGAA
481  ATGACCAGGG CCGTCAACGA CCTGGCGAAG AAGAAGAAGA TGGCGACACT GGAGGAGGAG
541  GAGGTGAAGA TGCAGATGCA GATGCCGGAG GCCGCTGATC TGGCGGCGGC GGCAGCGGCT
601  GACCCACAGG CCGACACGAA GAGCAAGCTG GTGAAGCTGG TGGTCATGGT GTGCGAGGGG
661  CTGCGGGTTCA ACACCGTGTC CCGCACGGTG GACGCGGGGT TCAACAGCCA GCACGGGGTG
```

FIG. 7 (CONT.)

```
 721  ACCTTGACCG TGACGCAGGG GAAGCAGGTG CAGAAGTGGG ACAGGATCTC CAAGGCGGCC
 781  TTCGAGTGGG CTGACCACCC CACCGCTGTG ATCCCCGACA TGCAGAAGCT TGGCATCAAG
 841  GATAAGAACG AAGCAGCGAG GATCGTTGCG CTCGTTAAGA ATCAAACTAC TGCCGCTGCC
 901  GCTACTGCTG CCAGTGCTGA CAACGACGAC GACGAGGCCT GATCAATGCA ACGACACATC
 961  ATGATCTGCT GCTGCACTTA ATTACTATGT TCGTATACAA ATAAATACAC CCGGCGTACG
1021  CGGTGTTCCT TATATGGTCT AAAATGTAGC CAGTAAATTT TAAACTACTT TCTCGTGCCG
1081  AATTCACTGG CCGGCATGCT ATATA
```

FIG. 9

```
1    GCTAATTAATTAAGCTTAAAAGGAGGAAAAAATT ATG GCC GAG ATA ACC CTA GAG
1                                      Met Ala Glu Ile Thr Leu Glu>

57   CCG AGT GAT CTT ATG GCG CAA ACA AAC AAA AGA ATA GTG CCA AAG TTC
8    Pro Ser Asp Leu Met Ala Gln Thr Asn Lys Arg Ile Val Pro Lys Phe>

105  ACT GAA ATC TTC CCC GTG GAG GAC GCG AAC TAC CCT TAC AGC GCC TTC
24   Thr Glu Ile Phe Pro Val Glu Asp Ala Asn Tyr Pro Tyr Ser Ala Phe>

153  ATC GCG TCG GTC CGG AAA GAC GTG ATC AAA CAC TGC ACC GAC CAT AAA
40   Ile Ala Ser Val Arg Lys Asp Val Ile Lys His Cys Thr Asp His Lys>

201  GGG ATC TTC CAG CCC CTG CCA CCG GAG AAG GTC CCG GAG CTA
56   Gly Ile Phe Gln Pro Val Leu Pro Pro Glu Lys Val Pro Glu Leu>

249  TGG TTC TAC ACA GAG CTC AAA ACT AGG ACC AGC TCC ATC ACG CTC GCC
72   Trp Phe Tyr Thr Glu Leu Lys Thr Arg Thr Ser Ile Thr Leu Ala>

297  ATA CGC ATG GAC AAC CTG TAC CTC GTG GGC TTC AGG ACC CCG GGC GGG
88   Ile Arg Met Asp Asn Leu Tyr Leu Val Gly Phe Arg Thr Pro Gly Gly>

345  GTG TGG GAG TTC GGC AAG GAC GGC GAC ACC CAC CTC CTC GGC GAC
104  Val Trp Glu Phe Gly Lys Asp Gly Asp Thr His Leu Leu Gly Asp>
```

FIG. 9 (CONT.)

| | | | | | | | | | | | | | | | | |
|---|---|---|---|---|---|---|---|---|---|---|---|---|---|---|---|---|
| 393 120 | AAC Asn | CCC Pro | AGG Arg | TGG Trp | CTC Leu | GGC Gly | TTC Phe | GGC Gly | AGG Arg | TAC Tyr | CAG Gln | GAC Asp | CTC Leu | ATC Ile | GGC Gly> |
| 441 136 | AAC Asn | AAG Lys | GGT Gly | CTG Leu | GAG Glu | ACC Thr | GTC Val | ACC Thr | ATG Met | GGC Gly | AGG Arg | GAA Glu | ATG Met | ACC Thr | AGG Arg> |
| 489 152 | GCC Ala | GTC Val | AAC Asn | GAC Asp | CTG Leu | GCG Ala | AAG Lys | AAG Lys | GCG Ala | CCA Pro | GAC Asp | GCT Ala | CCA Pro | CAG Gln | GCC Ala> |
| 537 168 | GAC Asp | ACG Thr | AAG Lys | AGC Ser | AAG Lys | CTG Leu | GTG Val | AAG Lys | CTG Leu | GTG Val | TGC Cys | GAG Glu | GGG Gly | GAG Glu | GGG Gly> |
| 585 184 | CTG Leu | CGG Arg | TTC Phe | AAC Asn | ACC Thr | GTG Val | TCC Ser | CGC Arg | ACG Thr | GTG Val | GAC Asp | GCG Ala | GGG Gly | TTC Phe | AAC Asn | AGC Ser> |
| 633 200 | CAG Gln | CAC His | GGG Gly | GTG Val | ACC Thr | TTG Leu | ACC Thr | GTG Val | ACG Thr | CAG Gln | GGG Gly | AAG Lys | CAG Gln | GTG Val | CAG Gln | AAG Lys> |
| 681 216 | TGG Trp | GAC Asp | AGG Arg | ATC Ile | TCC Ser | AAG Lys | GCG Ala | GCC Ala | TTC Phe | GAG Glu | TGG Trp | GCT Ala | GAC Asp | CAC His | CCC Pro | ACC Thr> |
| 729 232 | GCT Ala | GTG Val | ATC Ile | CCC Pro | GAC Asp | ATG Met | CAG Gln | AAG Lys | CTT Leu | GGC Gly | ATC Ile | AAG Lys | GAT Asp | AAG Lys | AAC Asn | GAA Glu> |

FIG. 9 (CONT.)

```
777  GCA GCG AGG ATC GTT GCG CTC GTT AAG AAT CAA ACT ACT GCC GCT GCC
248  Ala Ala Arg Ile Val Ala Leu Val Lys Asn Gln Thr Thr Ala Ala Ala>

825  GCT ACT GCT GCC AGT GCT GAC AAC GAC GAC GAG GCC TGA TCAATGC
264  Ala Thr Ala Ala Ser Ala Asp Asn Asp Asp Glu Ala END

874  AACGACACATCATGATCTGCTGCACTTAATTACTATGTTCCGTATACAAATAAATACACCC

937  GGCGTACGGGTGTTCCTTATATGGTCTAAAATGTAGCCAGTAAATTTAAACTACTTTCTCG

1000 TGCCGAATTCACTGGCCCGGCATGCTATATA
```

FIG. 10

```
1    GCTTAATTAATTAAGCTTAAAAGGAGGAAAAAATT ATG AAA AGA ATA GTG CCA
1                                       Met Lys Arg Ile Val Pro>

55   AAG TTC ACT GAA ATC TTC CCC GTG GAG GAC GCG AAC TAC CCT TAC AGC
7    Lys Phe Thr Glu Ile Phe Pro Val Glu Asp Ala Asn Tyr Pro Tyr Ser>

103  GCC TTC ATC GCG TCG GTC CGG AAA GAC GTG ATC AAA CAC TGC ACC GAC
23   Ala Phe Ile Ala Ser Val Arg Lys Asp Val Ile Lys His Cys Thr Asp>

151  CAT AAA GGG ATC TTC CAG CCC GTG CTG CCA CCG GAG AAG AAG GTC CCG
39   His Lys Gly Ile Phe Gln Pro Val Leu Pro Pro Glu Lys Lys Val Pro>

199  GAG CTA TGG TTC TAC ACA GAG CTC AAA ACT AGG ACC AGC TCC ATC ACG
55   Glu Leu Trp Phe Tyr Thr Glu Leu Lys Thr Arg Thr Ser Ser Ile Thr>

247  CTC GCC ATA CGC ATG GAC AAC CTG TAC CTC GTG GGC TTC AGG ACC CCG
71   Leu Ala Ile Arg Met Asp Asn Leu Tyr Leu Val Gly Phe Arg Thr Pro>

295  GGC GGG GTG TGG GAG TTC GGG AAG GAC ACC CAC CAC CTC CTC
87   Gly Gly Val Trp Trp Glu Phe Gly Lys Asp Gly Asp Thr His Leu Leu>

343  GGC GAC AAC CCC AGG TGG CTC GGC TTC GGC AGG TAC CAG GAC CTC
103  Gly Asp Asn Pro Arg Trp Leu Gly Phe Gly Arg Tyr Gln Asp Leu>
```

FIG. 10 (CONT.)

| | | | | | | | | | | | | | | | |
|---|---|---|---|---|---|---|---|---|---|---|---|---|---|---|---|
| 391 119 | ATC Ile | GGC Gly | AAC Asn | AAG Lys | GGT Gly | CTG Leu | GAG Glu | ACC Thr | GTC Val | ACC Thr | ATG Met | GGC Gly | CGC Arg | GCC Ala | GAA Glu | ATG Met> |
| 439 135 | ACC Thr | AGG Arg | GCC Ala | GTC Val | AAC Asn | GAC Asp | CTG Leu | GCG Ala | AAG Lys | AAG Lys | AAG Lys | GCG Ala | GCT Ala | GAC Asp | CCA Pro> |
| 487 151 | CAG Gln | GCC Ala | GAC Asp | ACG Thr | AGC Ser | AAG Lys | CTG Leu | GTG Val | AAG Lys | CTG Leu | GTC Val | ATG Met | GTG Val | TGC Cys> |
| 535 167 | GAG Glu | GGG Gly | CTG Leu | CGG Arg | TTC Phe | AAC Asn | ACC Thr | GTG Val | TCC Ser | CGC Arg | ACG Thr | GAC Asp | GCG Ala | GGG Gly | TTC Phe> |
| 583 183 | AAC Asn | AGC Ser | CAG Gln | CAC His | GGG Gly | CTG Leu | ACC Thr | TTG Leu | ACC Thr | GTG Val | ACG Thr | CAG Gln | GGG Gly | AAG Lys | CAG Gln | GTG Val> |
| 631 199 | CAG Gln | AAG Lys | TGG Trp | GAC Asp | AGG Arg | ATC Ile | TCC Ser | AAG Lys | GCG Ala | GCC Ala | TTC Phe | GAG Glu | TGG Trp | GCT Ala | GAC Asp | CAC His> |
| 679 215 | CCC Pro | ACC Thr | GCT Ala | GTG Val | ATC Ile | CCC Pro | GAC Asp | ATG Met | CAG Gln | AAG Lys | CTT Leu | GGC Gly | ATC Ile | AAG Lys | GAT Asp | AAG Lys> |
| 727 231 | AAC Asn | GAA Glu | GCA Ala | GCG Ala | AGG Arg | ATC Ile | GTT Val | GCG Ala | CTC Leu | GTT Val | AAG Lys | AAT Asn | CAA Gln | ACT Thr | ACT Thr | GCC Ala> |

FIG. 10 (CONT.)

```
775  GCT GCC GCT ACT GCT GCC AGT GCT GAC GCT GAC AAC GAC GAC GAG GCC TGA
247  Ala Ala Ala Thr Ala Ala Ser Ala Asp Ala Asp Asn Asp Asp Glu Ala END
823  TCAATGCAACGACACATCATGATCTGCTGCACTTAATTACTATGTTCGTATACAAATAAA
886  TACACCCGGGCGTACGCGGTGTTCCTTATATGGTCTAAAATGTAGCCAGTAAATTTAAACTAC
949  TTTCTCGTGCCGAATTCACTGGCCCGGCATGCTATATA
```

DNA ENCODING INACTIVE PRECURSOR AND ACTIVE FORMS OF MAIZE RIBOSOME INACTIVATING PROTEIN

TECHNICAL FIELD OF THE INVENTION

The present invention relates to a ribosome-inactivating protein, and to novel forms and compositions thereof.

BACKGROUND OF THE INVENTION

The following information is provided for the purpose of making known information believed by the applicants to be of possible relevance to the present invention. No admission is necessarily intended, nor should be construed, that any of the following information constitutes prior art against the present invention.

Ribosome-inactivating proteins (RIPs) are plant proteins that are capable of catalytically inactivating eukaryotic ribosomes and are consequently extremely potent inhibitors of eukaryotic protein synthesis. RIPs have been divided into two classes: type 1 and type 2 RIPs (see Barbieri and Stirpe (1982), *Cancer Surveys,* 1:489–520). Type 2 RIPs (or A-chains are covalently attached via a disulfide bond to lectin-like proteins (or B-chains) with an affinity for cell surface carbohydrates. The B-chain binds to the cell surface and facilitates subsequent cellular internalization of the RIP A-chain moiety, which results in rapid inactivation of protein synthesis and cell death. Type 2 RIPs are therefore extremely potent cytotoxins and animal poisons, the best studied example of which is ricin.

In contrast, type 1 RIPs characterized to date consist of a single polypeptide chain equivalent in activity to that of A-chain RIPs but lacking a covalently attached B-chain. Consequently, they are scarcely toxic to intact cells but retain their extreme potency against cell-free protein translation systems. Typical concentrations that inhibit cell-free protein translation by 50% ($IC_{50}$) are 0.5–10 ng/ml (0.16–33 pM). Until the discoveries detailed below, type 1 RIPs were a remarkably homogeneous class of basic proteins with Mr values of about 30,000. There is significant amino acid sequence homology between members of both type 1 and type 2 RIPs, and with the bacterial Shiga and Shiga-like toxins which also have the same mechanism of action (Hovde et al. (1988), *Proc. Natl. Acad. Sci. USA,* 85:2568–2572).

Where the effect of RIPs on ribosomes has been examined, both type 1 and type 2 RIPs possess a unique and highly specific N-glycosidase activity which cleaves the glycosidic bond of adenine 4324 of the ribosomal 28S RNA (Endo in *Immunotoxins* (1988), (ed.) Frankel).

Interest in RIPs has primarily focused on their use in construction of therapeutic toxins targeted to specific cells such as tumor cells by attachment of a targeting polypeptide, most frequently a monoclonal antibody (*Immunotoxins* (1988), supra. This mimics the binding functionality of the B-chain of type 2 RIPs but replaces their non-specific action with a highly selective ligand. Another recent potential use is in HIV therapy (see U.S. Pat. No. 4,869,903).

Type 1 RIPs are found in a great variety of dicot and monocot plants and they may be ubiquitous. They are often abundant proteins in seeds, roots or latex for example. Their in vivo function is unclear but it has been proposed that they may be antiviral (Stevens et al. (1981), *Experientia* 37:257–259) or antifungal (Roberts and Seltrennikkoff (1986), *Bioscience Reports,* 6:19–29) agents.

To date, one article has discussed the presence of an inhibitor of animal cell-free protein synthesis in maize, as well as other cereal crops (Coleman, W. H. and Roberts W. R. (1982), *Biochimica et Biophysica Acta,* 696:239–244. The preparation of the maize inhibitor was via ammonium sulfate precipitation and phosphocellulose column chromatography. It is generally believed that the inhibitor isolated from maize was pure. The reported molecular weight of the inhibitor was 23 kiloDaltons (kD), with a reported $IC_{50}$ of 50–100 ng/ml in an ascites cell-free protein synthesis assay.

However, while a maize-derived ribosome inhibitor, like other ribosome inhibitors would appear to be useful for construction of cytotoxic conjugates, no artisan to date has reported to have successfully used a maize RIP. This is somewhat surprising in view of the success achieved with RIPs from other plants, including cereals such as barley (Lambert et al. in *Immunotoxins,* (1988), supra).

There is interest for recombinantly expressing RIP in commonly employed host eukaryotic cells. However, as RIPs effectively inhibit protein synthesis in eukaryotic cells, a predictable problem is that heterologous expression of an RIP will result in host cell death. Thus, eukaryotic cells are generally not used as recombinant host cells. Although eukaryotic cells may be used in certain circumstances, the RIP must be constructed so as to be secreted prior to the cell experiencing toxicity (see EP 0 335 476 A2). Therefore, prokaryotic host cells are the preferred hosts. Prokaryotic host cells, however, have disadvantages such as the inability to glycosylate and properly fold heterologously expressed proteins.

It is thus an object of the invention to provide a method of preparing inactive forms of RIPs, in which an inactive RIP may be expressed by eukaryotic host cells and then converted to an active form.

It is yet another object of the invention to provide the DNA sequence of the gene encoding such inactive forms of RIP, as well as plasmids host cells and cell cultures containing such DNA sequence.

Other objects and advantages of the present invention will become apparent from the Detailed Description of the Invention presented hereunder.

It is to these objects to which the present invention is directed.

SUMMARY OF THE INVENTION

In one aspect, the present invention is directed to a homogeneous protein, termed a proRIP, wherein the protein is incapable of substantially inactivating eukaryotic ribosomes, but which can be converted into a protein that is capable of substantially inactivating eukaryotic ribosomes, termed an RIP, said proRIP having a removable, internal peptide linker sequence.

In a second aspect, the present invention is directed to a homogeneous protein of claim 1, wherein the proRIP has a removable, internal peptide linker selectively inserted in the amino acid sequence of RIP selected from the group consisting of maize RIP, barley RIP, ricin A-chain, saporin, abrin A-chain, SLT-, and trichosanthin.

In a third aspect, the present invention is directed to a homogeneous protein, wherein the protein is incapable of substantially inactivating eukaryotic ribosomes, termed a proRIP, but which can be converted into a protein that is capable of substantially inactivating eukaryotic ribosomes, termed an RIP, said proRIP having a removable, internal peptide linker sequence, wherein the linker is a sequence effectively homologous to the following amino acid sequence:

MATLEEEEVKMQMQMPEAADLAAAA.

In a fourth aspect, the present invention is directed to a homogeneous protein, wherein the protein is incapable of substantially inactivating eukaryotic ribosomes, termed a proRIP, but which can be converted into a protein that is capable of substantially inactivating eukaryotic ribosomes, termed an RIP, said proRIP having a removable, internal peptide linker sequence, has an amino acid sequence effectively homologous to the following sequence:

KRIVPKFTEIFPVEDANYPYSAFIASVRKDVIKHCTDHKGIFQPVLPPEKKVPELW
FYTELKTRTSSITLAIRMDNLYLVGFRTPGGVWWEFGKD
GDTHLLGDNPRWLGFGGRYQDLIGNKGLETVTMGRAEMTR
AVNDLAKKKKMATLEEEEVKMQMQMPEAADLAAAAAADPQADTKSKLVK
LVVMVCEGLRFNTVSRTVDAGFNSQHGVTLTVTQGKQVQKWDRIS
KAAFEWADHPTAVIPDMQKLGIKDKNEAARIVALVKNQTTAAAATAAS
ADNDDDEA.

In a fifth aspect, the present invention is directed to a homogeneous protein, wherein the protein is incapable of substantially inactivating eukaryotic ribosomes, termed a proRIP, but which can be converted into a protein that is capable of substantially inactivating eukaryotic ribosomes, termed an RIP, said proRIP having a removable, internal peptide linker sequence, and has an amino acid sequence effectively homologous to the following sequence:

MAEITLEPSDLMAQTNKRIVPKFTEIFPVEDANYPYSAFIASVRKDVIKHCTDHKG
IFQPVLPPEKKVPELWFYTELKTRTSSITLAIRMDNLYLVGFRTPGGVWWEFGKD
GDTHLLGDNPRWLGFGGRYQDLIGNKGLETVTMGRAEMTR
AVNDLAKKKKMATLEEEEVKMQMQMPEAADLAAAAAADPQADTKSKLVK
LVVMVCEGLRFNTVSRTVDAGFNSQHGVTLTVTQGKQVQKWDRIS
KAAFEWADHPTAVIPDMQKLGIKDKNEAARIVALVKNQTTAAAATAAS
ADNDDDEA.

In a sixth aspect, the present invention is directed to a homogeneous protein, wherein the protein is capable of substantially inactivating eukaryotic ribosomes, termed a maize RIP, said maize RIP having an amino terminal fragment, termed a 16.5K fragment and a carboxy terminal fragment, termed an 11.5K fragment, said 16.5 k fragment having an amino acid sequence effectively homologous to the following sequence:

KRIVPKFTEIFPVEDANYPYSAFIASVRKDVIKHCTDHKGIFQPVLPPEKKVPELW
FYTELKTRTSSITLAIRMDNLYLVGFRTPGGVWWEFGKD
GDTHLLGDNPRWLGFGGRYQDLIGNKGLETVTMGRAEMTR
AVNDLAKKKK and the 11.5K fragment having an amino acid sequence effectively homologous to the following sequence:

DPQADTKSKLVKLVVMVCEGLRFNTVSRTVDAGFNSQHGVTLTVTQGKQVQKWDRI
SKAAFEWADHPTAVIPDMQKLGIKDKNEAARIVAL
VKNQTTAAAATAASADNDDDEA.

In a seventh aspect, the present invention is directed to a DNA isolate encoding a protein capable of being converted into a ribosome inactivating protein, wherein the DNA isolate has a nucleotide sequence effectively homologous to the sequence set forth in FIG. 1.

In an eighth aspect, the present invention is directed to a DNA isolate encoding a fusion protein capable of inactivating ribosomes, wherein the DNA isolate has a nucleotide sequence effectively homologous to the sequence set forth in FIG. 7, but having nucleotides 520 to 594 inclusive deleted.

In other aspects, the invention is directed to expression vehicles capable of effecting the production of such aforementioned proteins in suitable host cells. It includes the host cells and cell cultures which result from transformation with these expression vehicles.

BRIEF DESCRIPTION OF THE FIGURES

FIG. 1 shows the nucleotide sequence and the deduced amino acid of the maize proRIP cDNA.

FIG. 3 shows a comparison of maize RIP and barley RIP amino acid sequences.

FIG. 4 shows a comparison of maize RIP and ricin A chain amino acid sequences.

FIG. 5a shows the alignment of the N-terminal amino acid sequence of the maize RIP 16.5 kD polypeptide with the N-termini of RIPs from from other sources.

FIG. 5b shows the alignment of maize RIP with regions of homology in the amino acid sequences of other RIPs.

FIG. 7 shows the R34 DNA sequence obtained by polymerase chain reaction (PCR) amplification of maize proRIP cDNA. The underlined sequences indicate the sequences of the primers used.

FIG. 9 shows the nucleotide sequence and the deduced amino acid sequence of R34-DL.

FIG. 10 shows the nucleotide sequence and the deduced amino acid sequence of R30-DL.

DETAILED DESCRIPTION OF THE INVENTION

Figure 2:
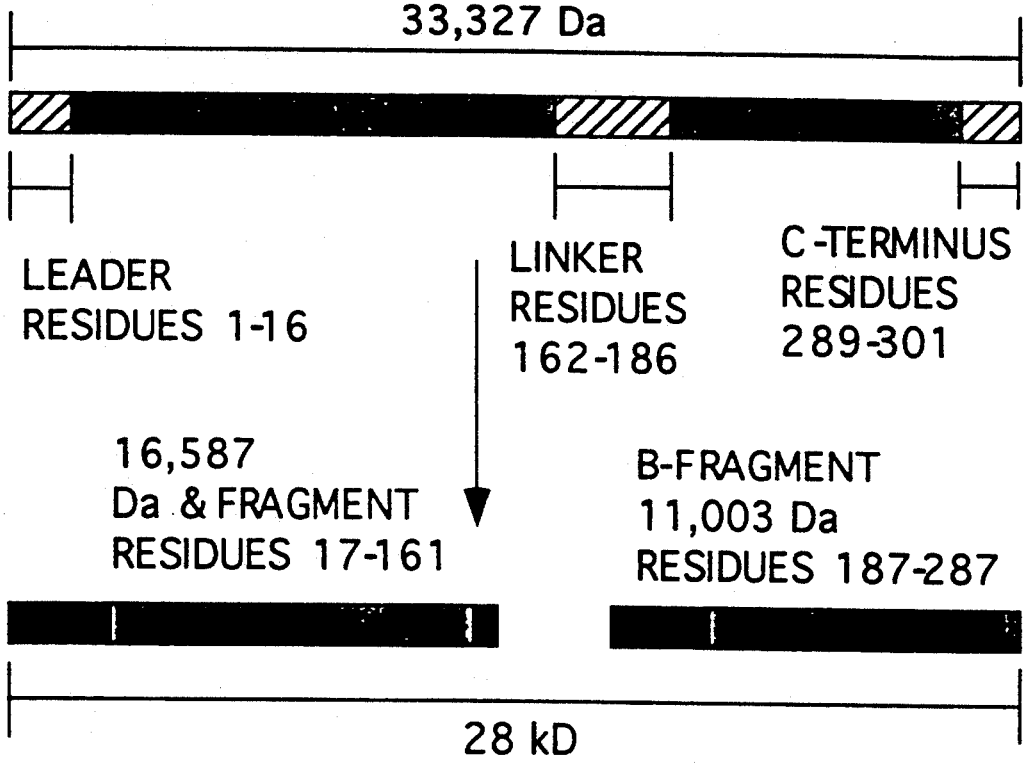
FIG. 2 shows a schematic representation of the processing of proRIP to the active form.
Figure 6:
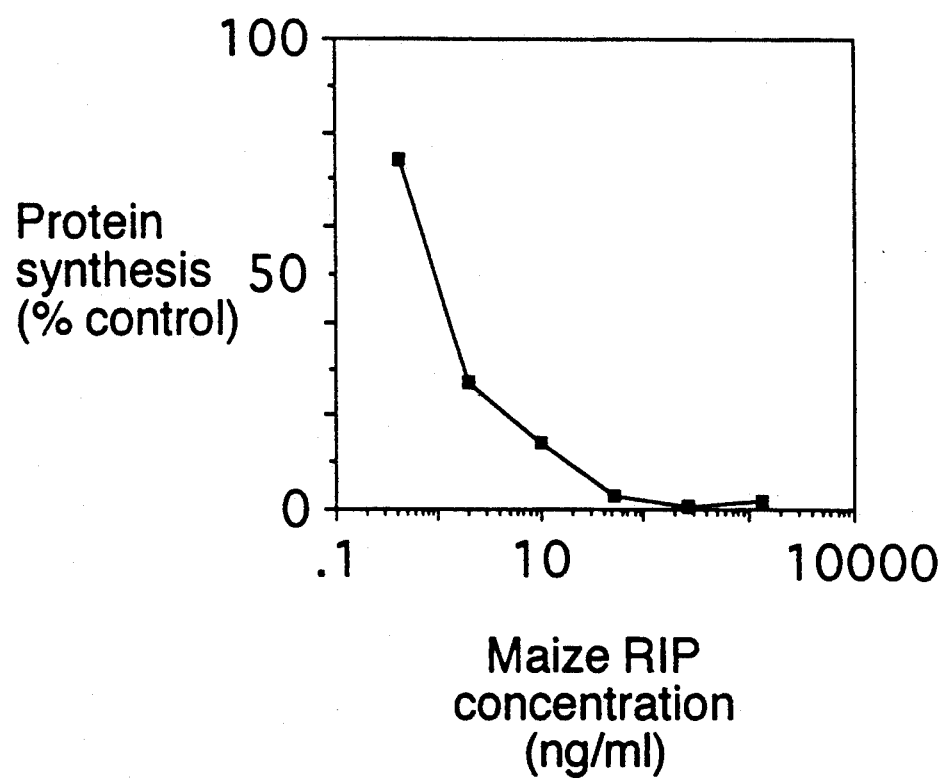
FIG. 6 shows the effect of maize RIP on mammalian cell-free protein synthesis.

The entire teachings of all references cited herein are incorporated by reference.

Definitions

Amino Acids

The single letter code for amino acids is set forth below:

| | | | |
|---|---|---|---|
| Glycine: | G | Phenylalanine: | F |
| Alanine: | A | Tyrosine: | Y |
| Valine: | V | Threonine: | T |
| Leucine: | L | Cysteine: | C |
| Isoleucine: | I | Methionine: | M |
| Serine: | S | Glutamic acid: | E |
| Aspartic acid: | D | Tryptophan: | W |
| Lysine: | K | Proline: | P |
| Arginine: | R | Asparagine: | N |
| Histidine: | H | Glutamine: | Q |
| Unknown | X | | |

"RIP" means a protein that is capable of catalytically inactivating eukaryotic ribosomes.

"proRIP" means a precursor protein that is not capable of catalytically inactivating eukaryotic ribosomes, but is capable of being proteolytically processed to yield an active RIP.

"Linker" refers to an internal amino acid sequence within a proRIP, whereby the linker is of a length and contains residues effective to render the proRIP incapable of catalytically inhibiting translation of a eukaryotic ribosome.

"$IC_{50}$" means the concentration of a protein necessary to inhibit protein synthesis by 50% in a cell-free protein synthesis assay.

"Cytotoxic" refers to the specific ability of RIPs to cause the death of cells against which they are targeted.

The term "target cells" means those cells having ribosomes which the maize RIP can inactivate. The target cells may be present in living organisms or they may be preserved or maintained in vitro. The cells may be individual or associated to form an organ. Exemplary target cells include any eukaryotic cell (e.g., mammalian, insect, fungal and plant cells).

The term "targeting vehicle" means a cell/tissue specific carrier moiety.

"Gene" refers to the entire DNA portion involved in the synthesis of a protein. A gene embodies the structural or coding portion which begins at the 5' end from the translation start codon (usually ATG) and extends to the stop (TAG, TGA or TAA) codon at the 3' end. It also contains a promoter region, usually located 5' or upstream to the structural gene, which initiates and regulates the expression of a structural gene and a 3' nontranslated region downstream from the translated region.

"Expression" refers to a two-part process for the transcription and translation of a structural gene. The DNA defining the gene is transcribed into a precursor RNA, which is processed to its mature form, the mRNA. During translation, the cell's ribosomes, in conjunction with transfer RNA (tRNA), convert the RNA "message" into proteins.

As used herein, "proRIP gene" means a DNA segment that codes for the proRIP.

PREFERRED EMBODIMENTS OF THE INVENTION

1. Maize RIP

Coleman and Roberts (1982), supra, described the partial purification of a protein synthesis inhibitor from maize. In part, the lack of success to date by skilled artisans in successfully utilizing the maize RIP described by Coleman and Roberts may be attributed to the fact that the protein synthesis inhibitor was relatively uncharacterized.

The inventors have succeeded in purifying an active RIP from maize. The maize RIP has an $IC_{50}$ of about 1 nanogram per milliliter (ng/ml) in a mammalian cell-free protein translation assay.

By purifying the maize RIP, the inventors were able to deduce that the maize RIP is in fact composed of two associated fragments of 16.5 kD and 11.5 kD. Polyclonal anti-sera against each fragment both crossreact with a polypeptide present in maize kernels having a molecular weight of about 34 kD as determined by the sodium dodecyl sulfate polyacrylamide-gel electrophoresis (SDS-PAGE) method of Laemmli ((1970), *Nature*, 22:680–685). This demonstrates that the two fragments of the maize RIP are in fact derived from a common precursor (maize proRIP).

Upon purification, the maize proRIP has insignificant ribosome inactivating ability, having an $IC_{50}$ of greater than 10 micrograms per milliliter ($\mu$g/ml) in a cell-free protein synthesis assay. This represents an activity of less than one-thousandth (1/1000) the activity of the active maize RIP.

Thus, the inventors have discovered that maize, surprisingly, has an active and inactive form of an RIP. Moreover, the inactive proRIP can be converted in vitro to the active form by treatment with a protease. This unexpected result therefore provides artisans with a unique activatable RIP.

The invention also enables the production of both forms of the maize proRIP and RIP via the application of recombinant DNA technology. This invention in turn allows the production of sufficient quality and quantity of material to create novel forms of the protein unimpeded by the restriction necessarily inherent in the isolation methods hitherto employed involving production and extraction of the protein from sources in nature.

The present invention relates to the discovery of the cDNA that encodes the maize proRIP (maize proRIP cDNA). It is believed that the cDNA clone encodes authentic maize proRIP. The recombinantly produced maize proRIP shares the following properties with the 34 kD RIP precursor protein isolated and characterized from nature: (1) portions of the amino acid sequence deduced from the cDNA nucleotide sequence are equivalent to amino acid sequences obtained directly from the RIP from nature; (2) the polypeptide encoded by the maize proRIP cDNA is recognized by anti-maize RIP antibodies; (3) the molecular weight of polypeptide encoded by the maize proRIP cDNA is in good agreement with the naturally occurring protein; (4) each protein exhibits relatively equivalent ribosome inactivating activity; and (5) each protein is convertable to a ribosome inactivating protein.

When the maize proRIP cDNA is inserted into an expression vector, the cDNA is useful to produce maize proRIP. The maize proRIP cDNA encodes the maize proRIP exclusive of irrelevant proteins that often are associated with the maize proRIP and RIP in nature.

The nucleotide sequence of the maize proRIP cDNA and the deduced amino acid sequence of such the corresponding maize proRIP is set forth in FIG. 1. Direct amino acid sequence analysis of the N and C-terminal amino acids of the 16.5K fragment and the N-terminus of the 11.5K fragment of active RIP purified from maize kernels has enabled the inventors to define four sequence segments in the proRIP amino acid sequence (FIG. 2): (1) a putative leader sequence, from residues 1 to 16, (2) the 16.5K fragment, from residues 17–156, (3) an internal linker sequence, from residues 157–182, and (4) the 11.5K fragment, from residues 183–301. The net charges of these polypeptides are as follows: proRIP, $+3$: leader $-3$: 16.5K, $+10$; linker, $-5$: 11.5K, $+1$. Loss of the leader and linker therefore results in a dramatic change in net charge of the protein from $+3$ to $+11$.

Maize proRIP as isolated from nature has an observed pI of 6.5 which agrees well with the value of 6.1 derived from the deduced amino acid sequence. The pI of the active maize RIP from nature is $\geq 9$, compared to the calculated value from the deduced amino acid sequence of 9.06 (i.e., after deletion of the acidic leader and linker sequences). Thus, the maize RIP has a basic pI, which is consistent with the pI of other RIPs.

The amino acid sequence of the maize proRIP can be compared with that of another RIP from a monocot source, barley (see FIG. 3). The upper sequence is maize RIP and the lower sequence is barley RIP taken from Asano et al. (1986), *Carlsberg Res. Commun.*, 51:129. Identical residues are denoted by a solid line and conservative substitutions by a dotted line, dashes indicate insertions to maximize homology. Residues are numbered on the left.

There is an overall homology of 28% (34% including conservative substitutions). However, the unique nature of the linker region of maize proRIP is clearly shown by the resulting gap that has been introduced in the barley sequence to maintain homology. A lower, but significant, degree of homology is seen when the maize proRIP sequence is compared to that of ricin A chain (see FIG. 4). The upper sequence is maize RIP and the lower sequence is ricin A chain taken from Lamb et al. (1985), *Eur. J. Biochem.*, 148:265. Identical residues are denoted by a solid line and conservative substitutions by a dotted line, dashes indicate insertions to maximize homology. Residues are numbered on the left, the numbering of the ricin sequence corresponds to that of the mature protein. A gap was again introduced in the ricin A sequence to maximize homology corresponding to the linker region of the maize proRIP (FIG. 4).

Further comparison of the maize proRIP sequence with published full-length sequences of other RIPs indicate that there are four regions of significant homology between these proteins (FIG. 5). The Glu 177, Arg 180, Asn 209 and Trp 211 of ricin A have been implicated in the active site region of the molecule (Robertus in *Immunotoxins* (1988), supra).

The first region is shown in FIG. 5A. FIG. 5a shows the alignment of the N-terminal amino acid sequence of the maize RIP 16.5 kD polypeptide with the N-termini of RIPs from from other sources. The sequences are taken from: barley RIP, Asano et al. (1986), supra; ricin A-chain, Lamb et al. (1985), supra; dodecandrin, Ready et al. (1985), *Biochem. Biophys, Acta*, 791:314: pokeweed anti-viral protein 2 (AP2), Bjorn et al. (1985), *Biochim. Biophys. Acta*, 790:154; Shiga-like toxin 1A (SLT-IA), Calderwood et al. (1987), *Proc. Nat. Acad. Sci. USA*, 84:4364: remaining sequences are set forth in Montecucchi et al. (1989), *Int. J. Peptide Res.*, 33:263. Positions showing homology in 8 or more sequences are noted by solid (identical residues) or dotted (conservative substitution) lines.

The other three regions are internally located, being set forth as shown in FIG. 5b. FIG. 5b shows the alignment of maize RIP with regions of homology in the amino acid sequences of other RIPs. The sequences are taken from: barley RIP, Asano et al. (1986), supra; ricin A-chain, Lamb et al. (1985), supra; abrin A chain, Funatsu et al. (1988), *Agric. Biol. Chem.* 52:1095: saporin-6, Benatti et al. (1989) *Eur. J. Biochem.*, 183:465; Shiga-like toxin 1A (SLT-1A), Calderwood et al. (1987), supra; trichosanthin, Xuejun and Jiahuai (1986), *Nature*, 321:477. Positions showing identity or conservative substitutions in four or more sequences are underlined, dashes indicate insertions to maximize homology. Vertical lines indicate residues that are conserved in all seven sequences. The starting amino acid of each sequence is indicated (note that trichosanthin contains an insertion at residue 67–76).

When the internal linker sequence of the maize proRIP is removed, the resultant maize RIP has significant ribosome inactivating activity. The activity has been found to be significant regardless of whether the leader sequence has been removed (e.g., by recombinant methods). However, the proRIP is most active when the leader sequence is also removed and probably when C-terminus residues are also removed. In nature, the linker is cleaved by endogenous proteases released by germinating maize seeds. Significantly, the inventors have discovered that the linker may also be cleaved in vitro by certain proteases, e.g., papain, to yield active maize RIP from the precursor. It is likely that papain mimics the effect of endogenous thiol proteases released on germination of the maize kernel.

It appears that, after removal of the internal linker, the two fragments of the processed polypeptide are held together by noncovalent forces. That is, the association of the two polypeptide chains does not depend upon interchain disulfide bonds or the formation of a peptide bond between the fragments.

Although not intended to be bound by theory, it is believed that the linker forms an external loop with exposed amino acid residues that are susceptible to proteolysis. Support for this suggestion comes from the alignment of the amino acid sequence of the maize proRIP with that of ricin A chain, the three dimensional structure of which is known Montfort (1987), *J. Biol. Chem.*, 262:5398. Based on this alignment, homologous residues of maize RIP can be positioned within the three dimensional structure of ricin A chain. The superimposed structures indicate that the C-terminal lysine of the 16.5K fragment (at residue 162) lines up with an externally positioned threonine (at residue 156) of the ricin A chain. Also the N-terminal alanine of the 11.5K fragment (at residue 189) lines up with an externally positioned glycine (at residue 157) of the ricin A chain.

2. Preparation of Maize proRIP and RIP.

Products of the present invention are characterized by freedom from association with contaminants which may be associated with the maize proRIP and RIP in their natural cellular environment or in extracellular fluids.

Homogeneous maize proRIP will have a molecular weight of about 34 kD, as determined by SDS-PAGE (see Laemmli (1970), supra), and will move as a single peak on ion exchange chromatography.

Homogeneous maize RIP will comprise two associated fragments having molecular weights of 16.5 kD and 11.5 kD, respectively, as determined by SDS-PAGE. The homogeneous protein will exhibit two dissociated peaks on reverse phase chromatography, and a single associated peak on ion exchange chromatography.

At the risk of over-simplification, it can be stated that the the following techniques may be employed to produce maize proRIP and RIP: (i) by isolation techniques of the amino acid and nucleotide sequences and (ii) "in vitro" synthesis of the amino acid and nucleotide sequences.

a. Purification from Maize

Because the physical properties of the maize proRIP and RIP have been set forth herein, skilled artisans may now, without undue experimentation, purify both the maize proRIP and RIP directly from mature and germinating maize seeds and developing maize kernels. Generally, the purification of the maize RIP and proRIP may be accomplished as follows.

Maize seeds or immature maize kernels may be homogenized to disrupt the individual kernels. This can be accomplished by any type of commercially available homogenizer.

The maize proRIP and/or RIP may be purified from the homogenization product by any appropriate protein purification technique. Exemplary techniques include gel filtration chromatographic techniques, such as conventional liquid chromatography, ion exchange chromatography, high performance liquid chromatography and reverse phase chromatography.

b. Chemical Synthesis

It is also possible to synthesize in vitro the maize proRIP and RIP from their constituent amino acids. Suitable techniques are the solid phase method, as described by Merrifield (1963), *J. Amer. Chem. Soc.*, 5:2149-2154. This solid phase method for synthesizing sequences of amino acids is also described in *Solid Phase Peptide Synthesis* (1969), (eds.) Stewart and Young. Automated synthesizers are also available, for example, from Applied Biosystems, Foster City, Calif.

The peptides thus prepared may be isolated and purified by procedures well known in the art (see *Current Protocols in Molecular Biology* (1989), (eds.) Ausebel, et al., Vol. 1) and Sambrook et al. (1989), *Molecular Cloning A Laboratory Manual.*

3. Preparation of Maize proRIP Gene

Because the cDNA sequence of the maize proRIP has been disclosed above, it is now possible to isolate the maize proRIP gene, without undue experimentation. The maize proRIP gene which is employed may be of chromosomal DNA, cDNA or synthetic origin or a combination of origins.

i. Purification from Maize

Maize cells containing the desired sequence may be isolated, and genomic DNA fragmented by one or more restriction enzymes. The genomic DNA may or may not include naturally-occurring introns. The genomic DNA digested with selected restriction endonucleases yields fragments containing varying numbers of base pairs (bp).

Specifically comprehended as part of this invention include genomic DNA sequences encoding allelic variant forms of the maize proRIP gene which may include naturally occurring introns. The allelic gene may be derived using a hybridization probe made from the DNA or RNA of the maize proRIP gene as well as its flanking regions. Flanking regions" are meant to include those DNA sequences 5' and 3' of the maize proRIP protein encoding sequences.

The DNA may be chemically synthesized by manual procedures (e.g., Caruthers (1983), In: *Methodology of DNA and RNA*, (ed.) Weissman); and automatic procedures (e.g., using an Applied Biosystems Model 380A DNA Synthesizer), and constructed by standard techniques of annealing and ligating fragments.

The DNA isolate encoding the maize proRIP gene may also be obtained from a cDNA library. mRNA may be isolated from a suitable source employing standard techniques of RNA isolation, and the use of oligo-dT cellulose chromatography to enrich the poly-A mRNA. A cDNA library is then prepared from the mixture of mRNA using a suitable primer, preferably a nucleic acid sequence which is characteristic of the desired cDNA. A single stranded DNA copy of the mRNA is produced using the enzyme reverse transcriptase. From the single stranded cDNA copy of the mRNA, a double-stranded cDNA molecule may be synthesized using either reverse transcriptase or DNA polymerase.

It is also possible to use primers to amplify the DNA from cells of appropriately prepared maize seeds and immature kernels by the polymerase chain reaction (PCR). PCR in essence involves exponentially amplifying DNA in vitro using sequence specified oligonucleotides. PCR is described in Mullis et al. (1987), *Meth. Enz.*, 155:335-350: *PCR Technology: Principles and Applications for DNA Amplification*, (ed.) Erlich (1989); and Horton et al. (1989), *Gene*, 77:61.

Thereafter, the desired sequences may be isolated and purified by procedures well known in the art (see *Current Protocols in Molecular Biology* (1989), supra) and Sambrook et al. (1989), *Molecular Cloning A Laboratory Manual.* ii. Chemical Synthesis

Component nucleotides may be synthetically assembled in vitro as outlined in Sambrook et al. (1989), supra. The DNA sequence may be assembled according to the well-established "genetic code", which specifies the codons for the various amino acids. Since there are 64 possible codon sequences but only twenty known amino acids, the genetic code is degenerate in the sense that different codons may code for the same amino acid.

5. Recombinant Techniques

Because of the relevance of recombinant DNA techniques, one need not be confined to the amino acid sequences of the naturally-occurring RIP.

Recombinant procedures make possible the production of effectively homologous proteins possessing part or all of the primary structural conformation and/or one or more of the biological properties of the maize RIP.

For purposes of this invention, an amino acid sequence is effectively homologous to a second amino acid sequence if at least 70%, preferably at least 80%, and most preferably at least 90% of the active portions of the amino acid sequence are identical. It is well known that some alterations in protein sequence may be possible without disturbing the functional abilities of the protein molecule, although other modifications are totally destructive.

Minor nucleotide modifications (e.g., substitution, insertions or deletions) in certain regions of the gene sequence can be tolerated and considered insignificant whenever such modifications result in changes in amino acid sequence that do not alter functionality of the final product. As can be seen in FIG. 5, RIPs for which a full-length sequence has been determined contain regions with significant homology. Similarly, as seen in FIG. 5, the N-terminal sequence similarities in an even greater number of RIPs has been compared. It is likely that these regions have particular effect upon the function of the respective RIP. Consequently, even minor nucleotide changes in such areas may not be tolerated as well as similar changes in nucleotides in other, less conserved regions.

General categories of potentially-equivalent amino acids are set forth below, wherein, amino acids within a group may be substituted for other amino acids in that group: 1 glutamic acid and aspartic acid: (2) lysine, arginine and histidine: (3) hydrophobic amino acids such as alanine, valine, leucine and isoleucine; (4) asparagine and glutamine: and (5) threonine and serine.

Exemplary techniques for nucleotide modification include using oligonucleotide site-directed mutagenesis and the polymerase chain reaction.

Oligonucleotide site-directed mutagenesis in essence involves hybridizing an oligonucleotide coding for a desired mutation with a single strand of DNA containing the region to be mutated and using the single strand as a template for extension of the oligonucleotide to produce a strand containing the mutation. This technique, in various forms, is described by Zoller et al. (1982), *Nuc. Acids Res..* 10:6487–6500: Norris et al. (1983), *Nuc. Acids Res.,* 11:5103–5112: Zoller et al. (1984), DNA, 3:479–488: and Kramer et al. (1982), *Nuc. Acids Res.,* 10:6475–6485.

Additionally, the oligonucleotides used in the PCR can have incorporated sequence alterations if desired to produce effectively homologous sequences. See Mullis et al. (1987), supra; *PCR Technology: Principles and Applications for DNA Amplification,* supra; and Horton et al. (1989), supra.

Thus more importantly, and critical to the definition, an effectively homologous RIP sequence to the RIP must retain the capacity to interact with and catalytically inactivate eukaryotic ribosomes, and an effectively homologous sequence to the proRIP must retain the capacity to be converted into an RIP.

(a) Recombinant Maize RIP

Methods and compositions are provided for producing heterologous polypeptides in a suitable host, whereby a completely heterologous, fused product is expressed. Thus, for example, in some instances (e.g., expression in prokaryotic host cells) it may be desirable to join the DNA sequence encoding the 16.5K fragment and the DNA sequence encoding the 11.5K fragment without an intervening sequence encoding a linker.

In preparing such a construction, it is necessary to bring the individual sequences together in such a way as to maintain the proper reading frame.

(b) Recombinant Maize proRIP

As with the maize RIP, the maize proRIP may be modified to produce effectively homologous proteins possessing part or all of the primary structural conformation and/or one or more of the biological properties of the maize proRIP.

Of course any modifications in the proRIP sequence that will alter the maize RIP must be consistent with the teachings set forth above. That is, the effectively homologous maize proRIP must have a linker sequence which, when cleaved, will yield a biologically functional maize RIP.

However, it is envisioned that, compared with changes to the RIP region, more significant changes may be made to the proRIP in the leader and linker regions. That is, since the leader and linker sequences are to be cleaved, the length and amino acid residues in their sequences may better be tolerated and considered insignificant, because it will not alter the functionality of the final product.

Further, the linker sequence of the proRIP need not be limited to the sequence set forth in FIG. 1. For example the length of the linker may be modified, provided that (1) the linker is cleavable, and (2) upon cleavage of the linker the resultant protein has an $IC_{50}$ value at least about 10 times lower than the $IC_{50}$ value of the protein containing the linker.

Primary criteria for selecting an effectively homologous linker include altering the net charge of the RIP (e.g., more acidic); creating a conformational shift in the protein or providing steric hindrance to the active site of the protein.

As noted previously, the maize RIP, like other RIPs, is basic. However, the maize proRIP has a slightly acidic pI. Thus, it is preferred that any effectively homologous linker will be primarily acidic.

The linker should be of a length which, while capable of altering the three dimensional structure of the Protein, will upon cleavage retain most of the three dimensional features of the active RIP molecule.

To ensure that the linker is cleavable it is generally required that the conformation of the proRIP be such that the linker cleavage sites be readily accessible to a selected cleavage agent.

Most commonly, cleavage will be effected outside of the replicative environment, for example, following harvest of microbial culture. Thus, when genetically modifying the maize proRIP, it may be preferable, in some instances, that the internal linker domain of the maize proRIP be retained, or altered so as to mimic the manner in which a natural, inactive proRIP liberates its active RIP fragments.

Any chemical or enzymatic means which recognizes a specific sequence and causes a specific cleavage can be utilized for the present invention. For example, it may be desirable to selectively include carboxy and amino termini of the linker sequences that are subject to cleavage with selected agents. For example, Pro-Xxx-Gly-Pro (where Xxx is unspecified) is selectively cleaved by collagenase, Ile-Glu-Gly-Arg by Factor Xa, and Gly-Pro-Arg by thrombin. Nilsson et al. (1988), In: *Advances in Gene Technology; Protein Engineering and Production,* (ed.) Brew et al.

A cleavage means is not suitable if its cleavage site occurs within the active RIP amino acid sequence. It is possible to select a specific cleavage sequence of only one amino acid residue so long as that residue does not appear in the active RIP sequence. It is preferred, however, to utilize a specific cleavage sequence which contains two or more amino acid residues sometimes referred to herein as an extended specific cleavage sequence. This type of sequence takes advantage of the extended active sites of various enzymes. By utilizing an extended specific cleavage sequence, it is highly probable that cleavage will only occur at the desired site and not within the desired protein.

The cleavage techniques discussed here are by way of example and are but representative of the many variants which will occur to the skilled artisan in light of the specification.

In some instances it may prove desirable to effect cleavage within the cell. For example, cloning vehicles with appropriate promoters could be provided with DNA coding for enzymes which convert the proRIP to the active form, operating in tandem with the other DNA coding expression of the proRIP.

(c) Preparation of Non-Maize proRIPs

Moreover, the present invention is not intended to be limited to novel constructions of maize proRIP. RIP having known amino acid sequences may now be altered into inactive forms by the insertion of a linker. The art has discussed the study of proteins in three dimensions, and has suggested modifying their architecture (see, for example, Van Brunt (1986), *Biotechnology*, 4:277-283).

Based on the information deduced from the maize system set forth herein, it now becomes possible to engineer inactive forms of any RIP having a three dimensional structure similar to the three dimensional structure of ricin A chain. The first step involves selecting plausible sites on the RIP between which the linker may be inserted. One of those sites is the exposed amino acid residues surrounding residue 156 of ricin A chain or its equivalent in other RIP sequences. Thus, the present invention is intended to encompass the insertion of a peptide linker in those sequences, provided that the insertion of the linker substantially reduces the ribosome inactivating ability of the RIP. By "substantially reduce" is meant that the insertion of a cleavable linker into an active RIP lowers the $IC_{50}$ value of the resultant protein by at least 10fold, preferably 100-fold, and more preferably 1000-fold.

As stated previously, ricin A chain has been shown to have sequence homology to many single chain RIPs. The RIPs set forth in FIG. 5 are intended for exemplification purposes only. RIPs characterized in the future that meet the above criteria are also considered to be a part of this invention.

Generally, the linker may be of a length, may be of an amino acid sequence, and may be internally positioned so as to substantially reduce the ribosome inactivating activity of the RIP.

Obviously, since the maize linker is the only known RIP linker found in nature, it is expected that such an amino acid sequence will logically be a primary candidate for insertion into other RIPs. However, as with maize, the present invention is intended to encompass linkers having effectively homologous sequences to the maize linker. The factors to be considered in synthetically preparing effectively homologous linkers for RIPs generally are the same as set forth above for selecting effectively homologous linkers for the maize linker.

Further, as is well known, protein sequences may be modified by post-translation processing such as association with other molecules, for example, glycosides, lipids, or such inorganic ions as phosphate. The ionization status will also vary depending on the pH of the medium or the the pH at which crystallization or precipitation of the isolated form occurs. Further, the presence of air may cause oxidation of labile groups, such as —SH. Included within the definition of the maize pro-RIP and fragments thereof are all such modifications of a particular primary structures, e.g., both glycosylated and non-glycosylated forms, neutral forms, acidic and basic salts, lipid or other associated peptide forms, side chain alterations due to oxidation or derivatization, and any other such modifications of an amino acid sequence which would be encoded by the same genetic codon sequence.

6. Cloning and Expression

Once a final DNA construction is derived, the expression vehicle in which it is contained may be used to transform an appropriate host cell to achieve expression in significant quantity.

a. Vectors

By appropriate choice of restriction sites, the desired DNA fragment may be positioned in a biologically functional vector which may contain appropriate control sequences not present in the selected DNA fragment. By "biologically functional" is meant that the vector provides for replication and/or expression in an appropriate host, either by maintenance as an extrachromosomal element or by integration into the host genome. A large number of vectors are available or can be readily prepared, and are well known to skilled artisans.

In general, vectors containing the appropriate promoters, which can be used by the host organism for expression of its own protein, also contain control sequences, ribosome binding sites, and transcription termination sites. Generally, the replicon and control sequences which are derived from species compatible with the host cell are used in connection with these hosts.

Finally, the vectors should desirably have a marker gene that is capable of providing a phenotypical property which allows for identification of host cells containing the vector.

b. Preparation of Vectors

Construction of suitable vectors containing the desired coding and control sequences may be produced as follows.

The means for inserting the DNA fragments containing the proRIP gene into vector includes using restriction endonucleases. Exemplary restriction enzymes include Aat II, Bam HI, Eco RI, Hind III, Nde I, Spe I, Xba I, Sac I, Bgl II, Pst I, Sal I and Pvu II.

Cleavage is performed by treating the vector with a restriction enzyme(s). In general, about 10 pg vector or DNA fragments is used with about 10 units of enzyme in about 100 μl of buffer solution. Endonuclease digestion will normally be carried out at temperatures ranging from about 37 degrees Centigrade (37° C.) to 65° C., at a pH of about 7 to about 9. (Appropriate buffers and substrate amounts for particular restriction enzymes are specified by the manufacturers.) Time for the reaction will be from about 1 to about 18 hours.

After the restriction enzyme digestion is complete, protein may be removed by standard techniques (e.g., extraction with phenol and chloroform). The nucleic acid may be then recovered from the aqueous fraction by standard techniques.

The desired fragment is then purified from the digest. Suitable purification techniques include gel electrophoresis or sucrose gradient centrifugation. The vector and foreign DNA fragments may then be ligated with DNA ligase.

An appropriately buffered medium containing the DNA fragments, DNA ligase, and appropriate cofactors is employed. The temperature employed will be between about 4° C. to about 25° C. When DNA segments hydrogen bond, the DNA ligase will be able to introduce a covalent bond between the two segments. The time employed for the annealing will vary with the temperature employed, the nature of the salt solution, as well as the nature of the sticky ends or cohesive termini. Generally, the time for ligation may be from 5 to 18 hours. See Sambrook et al. (1989), supra.

c. Host Cells

Thereafter, the vector constructions may be used to transform an appropriate host cell. Suitable host cells include cells derived from unicellular as well as multicellular organisms which are capable of being grown in cultures or by fermentation.

Various unicellular microorganisms can be used for both cloning and expression. Prokaryotes include members of the Enterobacteriaceae, such as strains of *Escherichia coli*, and Salmonella; Bacillaceae, such as *Bacillus subtilis*; Pneumococcus, Streptococcus, and *Haemophilus influenzae*.

In addition to prokaryotes, eukaryotic cells may be employed. As previously stated, eukaryotic cells have not heretofore been used as recombinant host cells for RIPs. By providing inactive forms of RIPs, the present invention provides skilled artisans with the flexibility to use eukaryotic cells as recombinant hosts. By transforming eukaryotic cells with the proRIP gene, the protein may be expressed at high levels without being toxic to the host cell. Since the protein is lacking in bioactivity pending extra-cellular cleavage, the effect is to enhance the biosafety of the procedure. The proRIP could then be selectively chemically or enzymatically converted to the desired RIP.

Exemplary eukaryotic microbes include yeast. *Saccharomyces cerevisae*, or common baker's yeast, is the most commonly used among eukaryotic microorganisms, although a number of other hosts are commonly available.

In addition to eukaryotic microbes, cultures of cells derived from multicellular organisms may also be used as hosts.

Examples of useful host mammalian cell lines are Sp2/0, VERO and HeLa cells, Chinese hamster ovary (CHO) cell lines, and W138, BHK, COS-7 and MDCK cell lines.

Other suitable hosts and expression systems are the baculovirus systems maintained in cultured insect cells, e.g., from *Spodoptera frugiperda.*

Finally, cells from and portions of higher plants have been found useful as recombinant hosts, and appropriate control sequences are available for expression in these systems. Suitable plant cells include cells derived from, or seedlings of, tobacco, petunia, tomato, potato, rice, maize and the like.

d. Transformation of Host Cells

Transformation of host cells may be accomplished by conventional techniques into host cells for expression of the desired protein. Conventional technologies for introducing vectors into living cells include particle bombardment technology, microinjection mechanisms, infectious agents, and techniques for protoplast transformation (e.g., electroporation, chemically-induced DNA uptake mechanisms, and fusion).

When expressing the maize RIP, the DNA fragments encoding the 16.5K fragment and the 11.5K fragment may be inserted into separate vectors, or into the same vector. Specifically, when the 16.5K and 11.5K fragments are contained in separate vectors, the host cells may be transformed via either cotransformation or targeted transformation.

e. Selection and Expression of Transformed Host Cells

Generally, after transformation of the host cells, the cells may be grown for about forty-eight (48) hours to allow for expression of marker genes. The cells are then placed in selective medium and/or screenable media, where untransformed cells are distinguished from transformed cells, either by death or a biochemical property.

The transformed cells are grown under conditions appropriate to the production of the desired protein, and assayed for expression thereof. Exemplary assay techniques include enzyme-linked immunosorbent assay, radioimmunoassay, or fluorescence-activated cell sorter analysis, immunohistochemistry and the like.

Selected positive cultures are subcloned in order to isolate pure transformed colonies. A suitable technique for obtaining subclones is via the limiting dilution method.

Uses of the Invention

By providing inactive precursor forms of the RIP, the inventors have provided protein synthesis inhibitors with uses in practical and improved ways not before possible. The inactive form of the RIP offers the additional advantage, over active RIPs, of not being active until removal of the linker sequence.

Moreover, essentially all of the uses that the prior art has envisioned for RIPs are intended for the novel maize RIP set forth herein. See, for example, *Immunotoxins* (1988), Frankel (ed.) and U.S. Pat. No. 4,869,903.

Although the maize RIP is not toxic to the majority of mammalian cells it can be made specifically cytotoxic by attachment to a targeting vehicle which is capable of binding to target cells.

Exemplary targeting vehicle include any peptide hormone, growth factor, or other polypeptide cell recognition protein for which a specific receptor exists. A few examples include antibodies and antibody fragments, lectins, insulin, glucagon, endorphins, growth hormone, melanocyte-stimulating hormone, transferrin, bombesin, low density lipoprotein, luteinizing hormone and asialoglycoprotein that bind selectively to target cells. See *Immunotoxins* (1988), supra. It is well established that conjugates which contain RIP exhibit maximal cytotoxicity only when the RIP moiety is released from the targeting vehicle.

Since the maize RIP does not contain a reactive sulfhydryl group, it is necessary to modify the proteins using chemical crosslinking reagents in order to link such maize RIP to targeting vehicles.

Conjugates of a monoclonal antibody and the maize RIP may be made using a variety of bifunctional protein coupling agents. General examples of such reagents are N-succinimidyl-3-(2-pyridyldithio) propionate, 2-iminothiolane, bifunctional derivatives of imidoesters such as dimethyl adipimidate, active esters such as disuccinimidyl suberate, aldehydes such as glutaraldehyde, bis-azido compounds such as bis(p-diazoniumbenzoyl)ethylenediamine, diisocyanates such as toluene 2,6-diisocyanate, and bis-active fluorine compounds such as 1,5-difluoro-2,4-dinitrobenzene. See, for example, WO 86/05098, the teachings of which are hereby incorporated by reference.

In addition, recombinant DNA methodologies may be employed to construct a cytotoxic fusion protein. For a general discussion of chimeric toxins, see, for example, Pastan and FitzGerald (1989), *The Journal of Biological Chemistry,* 264:15157-15160; and U.S. Pat. No. 4,892,827. These references teach modified Pseudomonas exotoxins which comprise a deletion in a receptor binding domain to form a fusion protein capable of rendering the modified toxin less toxic to selected cells. These references teach DNA sequences encoding the human alpha transforming growth factor (α-TGF) or human interleukin fused to toxin geness.

EXAMPLES

The present invention is illustrated in further detail by the following examples. The examples are for the purposes of illustration only, and are not to be construed as limiting the scope of the present invention. All temperatures not otherwise indicated are Centigrade. All parts and percentages are by weight unless otherwise specifically noted.

1. Rabbit Reticulocyte Cell-Free Protein Synthesis Assay

The inhibitory activity of the maize RIP toward mammalian protein synthesis is measured in a rabbit reticulocyte lysate system based on Pelham and Jackson (1976), *Eur. J. Biochem.,* 67:247-256.

A mix of the following reagents is prepared (2.5 ml total volume): 125 μl 200 mM Tris-HCl, pH 7.6+40 mM magnesium acetate+1.6M potassium chloride: 12.5 μl 3 mM hemin hydrochloride in 50% ethylene glycol; 1.0 ml untreated rabbit reticulocyte lysate (commercially available from Promega, Madison, Wis.): 1.0 ml $H_2O$: 62.5 μl amino acid mix; 125 μl 20 mM ATP+4 mM GTP: 125 μl 200 mM creatine phosphate: 50 μl 2.5 mg/ml creatine phosphokinase in 50% ethylene glycol. The amino acid mix contained 50 μM of each amino acid except glycine (100 μM), arginine, isoleucine, methionine and tryptophan (10 μM each) and contained no leucine. All stock solutions are previously adjusted to pH 7.5 prior to addition.

Five microliters 5 μl) of appropriate dilutions of samples to be assayed are placed in the wells of a 96-well plate and 50 μl of the mix added. After 10 minutes, 50 nanoCuries (nCi) $^{14}C$-leucine in 10 μl is added to each well. After a further 10 min, the reaction is quenched with 10 μl 1.5M potassium hydroxide and incubated for 45 min. 25 μl of each sample is then pipetted onto individual 2.1 cm Whatman 3 MM paper disks (commercially available from Whatman, Clifton, N.J.) and after drying for 2-3 min, the disks are washed successively by swirling in a flask with 250 ml 10% trichloroacetic acid, 250 ml 5% trichloroacetic acid (twice), 125 ml ethanol, 250 ml 1:1 ethanol/acetone, and 125 ml acetone. After drying, the filters are placed in vials with 10 ml scintillation cocktail and counted.

A. Isolation of Maize RIP

1. Protocol

All steps are performed at 4° C., except for HPLC which is performed at room temperature. Five hundred grams (500 g) of finely ground mature maize kernels are extracted for at least 2 hour and up to 24 (hr) with 1500 ml 25 mM sodium phosphate, pH 7.2 (PB)+50 mM sodium chloride. After the extract is strained through several layers of cheesecloth, the protein precipitating between 55% and 85% ammonium sulfate is collected and redissolved in PB, then dialyzed overnight against the same buffer. The solution is clarified by centrifugation and applied to a 2.5×10 centimeter (cm) DE-52 cellulose column equilibrated with PB. The protein passing straight through the column is collected and applied to a Mono S 10/10 column (Pharmacia LKB, Piscataway, N.J.) equilibrated with PB, and eluted with a linear gradient of 0-200 mM sodium chloride in PB over 90 min at 2 milliliter/ minute (ml/min). Alternatively, the protein can be precipitated with 85% ammonium sulfate and dialyzed overnight before applying to the Mono S 10/10 column.

Fractions containing ribosome inactivating protein activity (as measured by rabbit reticulocyte protein synthesis assay, described above) are pooled and concentrated to 0.5 ml in Centricon-10 devices (commercially available from Amicon, Danvers, Mass.), and applied to a Superose 12 column equilibrated in PB (commercially available from Pharmacia LKB) at a flow-rate of 0.4 ml/min. Fractions containing ribosome inactivating protein activity (as measured by a rabbit reticulocyte protein synthesis assay, described above) (the first major peak) are pooled. At this stage, the RIP is usually quite pure as identified by SDS-PAGE (see Laemmli (1970), supra). If necessary, further purification can be achieved by applying the protein to a Mono S 5/5 column (Pharmacia LKB) equilibrated with PB and eluting at 1 ml/min with 0-50 mM sodium chloride in PB over 5 min, then 50-200 mM sodium chloride in PB over 25 min.

Results from a typical purification are presented in Table 1. The effect of purified maize RIP on mammalian protein synthesis is shown in FIG. 6.

2. Antisera and Western Blot Analysis

The 16.5K and 11.5K polypeptide bands are cut from 3 millimeter (mm) SDS-PAGE gels after brief staining with Coomassie blue and are electroeluted using an electroelution device (commercially available from Bio-Rad, Richmond CA) according to the manufacturer's directions. The polypeptide preparations are then used to immunize rabbits to yield polyclonal anti-sera (prepared by RIBI Immunochem, Montana).

Western blots from Phastgels (commercially available from Pharmacia LKB, Piscataway, N.J.) are performed by removing the gel from the plastic backing and then electroblotting onto Immobilon paper (commercially available from Whatman, Clifton, N.J.). Blots are developed using the maize RIP primary antiserum at 1:2000 dilution and alkaline phosphatase-conjugated goat anti-rabbit secondary antibody from Bio-Rad, according to the manufacturer's instructions.

B. Isolation of Maize proRIP

The polyclonal antisera against the 16.5K and 11.5K fragments are used to identify a common 34 kD precursor polypeptide in crude extracts of maize kernels (maize proRIP). The presence of the maize proRIP can be monitored during subsequent purification by Western blot analysis as set forth above.

The purification of the maize proRIP is carried out as set forth below. All steps of the purification are performed at 4° C., except for HPLC which is performed at room temperature.

Two hundred fifty grams (250 g) of immature maize kernels are homogenized in 600 ml 25 mM sodium phosphate, pH 7.2 (PB)+5 µg/ml antipain. After the extract is strained through several layers of cheesecloth, the protein precipitating between 45 and 80% ammonium sulfate is collected and redissolved in 15 ml PB, then passed over a 2.5×15 cm Sephadex G-25 column (Pharmacia LKB) equilibrated in PB. Fractions containing protein are pooled and diluted to ~60 ml with water. The solution is applied to a Q-Sepharose (fast-flow) column packed in a 10/10 FPLC column (commercially available from Pharmacia LKB, Piscataway, N.J.) equilibrated with PB, and eluted with a 0–300 mM NaCl gradient at 2 ml/min over 75 min. Fractions containing the 34 kD precursor are pooled and concentrated by Centriprep 10 device (commercially available from Amicon) to 1.5 ml. This is diluted four-fold with water and applied to a Mono Q 5/5 column (commercially available from Pharmacia LKB) equilibrated in PB. The column is eluted with a 0–250 mM NaCl gradient over 60 min. Fractions containing the 34 kD polypeptide are pooled, concentrated to 0.5 ml and applied to a Superose 12 column (commercially available from Pharmacia LKB) equilibrated in PB. The major peak from this column contains the 34 kD maize RIP precursor and appropriate fractions are pooled and stored at −20° C.

C. PAGE Analysis of Maize RIP and proRIP

SDS-PAGE is performed with a Phastsystem ™ (commercially available from Pharmacia LKB) using 20% Phastgels and following the manufacturer's instructions. Native PAGE is performed at pH 4.2 as described in Pharmacia Phastsystem application file no. 300, method 1.

SDS-PAGE of highly purified, active maize RIP exhibits two polypeptides at 16.5 kD and 11.5 kD under both reducing and non-reducing conditions. A single band is seen in native PAGE analysis of purified, active maize RIP. The minimal Mr value of the associated, native maize RIP is therefore 28 kD.

By SDS-PAGE, highly purified maize proRIP migrates with a value of 34 kD.

D. In vitro Activation of Maize proRIP by Papain

A purified sample of proRIP is incubated at 0.5 mg/ml with papain, a plant thiol protease, at 0.01 mg/ml in sodium acetate buffer, pH 6 containing 2 mM dithiothreitol. After 1–2 hours at room temperature, the 34 kD proRIP is digested to a stable product exhibiting a polypeptide pattern almost identical to that of native, active maize RIP. There is a concomitant increase in ribosome inactivating activity in the incubation: the undigested proRIP has no ribosome inactivating activity up to 2 µg/ml, whereas papain-treated proRIP has an $IC_{50}$ of <80 ng/ml. In contrast trypsin has no effect on maize proRIP.

E. Chemically-determined Amino Acid Sequences

1. Maize RIP 16.5K and 11.5K N-Terminal Amino Acid Sequences

A sample of maize RIP is electrophoresed by the method of Laemmli (1970), supra, in 1.5 mm thick gels and the gel electroblotted onto Immobilon PVDF paper (commercially available from Whatman) using a Transphor ™ apparatus (commercially available from Pharmacia LKB). The paper is stained briefly with Coomassie blue and the bands corresponding to the 16.5 and 11.5 kD polypeptides cut out. These are N-terminal sequenced directly from the PVDF paper using an 470A gas phase sequencer (commercially available from Applied Biosystems, Foster City, Calif.). The following data is obtained (bracketed residues denote lower confidence assignments):

N-terminal sequence of 16.5 kD fragment:

```
K R I V P K I T E I F P V E D A N Y P V S A F
I A[G]V X K D V I
```

An additional minor species (~20% of the total species) had an N-terminal sequence of:

```
A Q T N K L]I V P K
```

N-terminal sequence of 11.5 kD fragment:

```
A A D P Q A D T K S X L V K L V V M S/C E
G L X F N T V S
```

2. 16.5K C-Terminal Amino Acid Sequence

The carboxy-terminal amino acid sequence of the 16.5 kD maize RIP polypeptide is determined using sequencing grade carboxypeptidase P from *Penicillium japonicum* (commercially available from Boehringer Mannheim, Indianapolis, Ind.). A sample of 16.5 kD polypeptide is purified by reverse-phase HPLC using a Vydac 5µ C4 4.6×30 mm RP column. The column is equilibrated with 0.1% trifluoroacetic acid (TFA), and eluted with 0–40% of 0.1%+80% acetonitrile over 8 min, then 40–60% of 0.1% TFA+80% acetonitrile over 20 min. The 11.5 kD polypeptide elutes after 21.9 minutes and the 16.5 kD polypeptide elutes after 23.3 minutes.

A lyophilized sample of the 16.5K polypeptide is dissolved in 20 mM sodium acetate, pH 5.8+4M urea. The digestion mix contains the following in 0.1 ml: 1.6 µg carboxypeptidase P, 66 µg 16.5 kD polypeptide, 0.12M sodium acetate pH 4.2, 0.8M urea. After 1, 5, 15, 60, 120 and 480 min, duplicate 8 µl aliquots from the digestion are added to 8 µl 1 0.4M sodium borate, pH 10.5 and frozen on dry ice. Amino acid analysis is performed essentially as described by Jones, In: *Methods of Protein Microcharacterization* (1986) ed. J. E. Shively.

The following sequence is obtained: NH₂-Asp-Leu-Ala-(Lys)n-COOH, where n=2–4. This is the carboxy terminus of the 16.5 kD polypeptide, therefore this and the N-terminus sequence of the 11.5 kD fragment define the linker region contained in the precursor (see amino acid sequence derived from cDNA in FIG. 1).

3 Maize proRIP N-Terminal Amino Acid Sequence

No N-terminal sequence data is obtained from a sample of the 34 kD maize proRIP indicating that this polypeptide is N-terminal blocked.

F. Isolation and Characterization of cDNA for Maize proRIP

1. Isolation

Immature kernels from field grown Pioneer hybrid 3737 are harvested, shelled from the cob, and stored at −20° C. Ten grams (10 g) kernels are frozen in liquid nitrogen for several minutes then ground to a powder in a Waring blender. The powder is suspended in 20 ml of ice cold TENS buffer (10 mM Tris pH 7.4, 1 mM EDTA, 0.5% SDS, 0.3M NaCl) and extracted immediately with an equal volume of phenol-chloroform-isoamyl alcohol (25:24:1) saturated with TENS buffer. The aqueous phase is collected and extracted three more times with fresh phenol mixtures.

Nucleic acids are precipitated from the aqueous phase by adjusting it to 0.3M sodium acetate pH 5.5 and adding 2.5 volumes of 100% ethanol. Nucleic acids are collected by centrifugation and suspended directly in 1 ml phenol-chloroform-isoamyl alcohol plus 1ml TENS and extracted by vortexing. The nucleic acid is precipitated from the aqueous phase by ethanol precipitation as above. The precipitate is collected by centrifugation and resuspended in TE buffer (10 mM Tris pH 7.4, 1 mM EDTA). Single strand nucleic acid is precipitated by adjusting the solution to 2M LiCl and incubating 4–12 hours at 4° C. Centrifugation yields a pellet which consisted of 2.2–2.5 mg of total RNA.

Poly(A)-containing RNA is enriched from the total RNA sample by using Hybond mAP purification mRNA affinity paper (commercially available from Amersham Corporation, Arlington Heights, Ill.). The supplier's protocol is followed. Typically 5–10 ug of poly(A) enriched RNA are recovered per milligram of total RNA.

Five micrograms (5 ug) of poly(A) enriched RNA were converted into double stranded cDNA using a cDNA Synthesis Kit (commercially available from Pharmacia, Piscataway, N.J., item #27-9260-01). The cDNA is ligated into the cloning vector Lambda gt11 (commercially available from Stratagene Inc., La Jolla, Calif.) following the supplier's instructions. Packaging of the ligated vector-insert mixture was done with the Gigapack plus packaging extract (commercially available from Stratagene Inc., La Jolla, Calif.) again following the suppliers protocol.

The PicoBlue Immunodetection Kit (commercially available from Stratagene, La Jolla, Calif.) is used to screen the Lambda gt11 maize kernel cDNA library using rabbit polyclonal antisera raised against the maize RIP, as described above.

Positive clones are purified to homogeneity and the cDNA inserts characterized by Eco RI restriction enzyme analysis. One of the largest Eco RI generated cDNA inserts (about 1,100 bp) is ligated into the Eco RI site of plasmid pUC19 (commercially available from Bethesda Research Labs (BRL), Gaithersberg, Md.). Clones carrying the RIP cDNA insert in both orientations are identified by restriction digestion and used for large scale plasmid purification.

2. Sequencing the Maize proRIP cDNA

The nucleotide sequence of the proRIP cDNA (FIG. 1) is determined by dideoxy chain termination sequencing using the Sequenase DNA sequencing kit (commercially available from United States Biochemical Corp., Cleveland, Ohio 44122). The double stranded pUC19-RIP is used as template following the manufacturer's instructions. The first round of sequencing is initiated by the M13/pUC forward sequencing primer (commercially available from BRL, Gaithersburg, Md.). Subsequent primers are derived from the sequenced maize proRIP cDNA. Both strands of the cDNA are fully sequenced at least once.

The open reading frame encoding the RIP protein is confirmed by comparing the cDNA deduced amino acid sequence (FIG. 1) to the chemically determined protein sequence data.

Expression of Maize proRIP and Derivatives in *Escherichia coli*

Various genetic derivatives of maize proRIP may be expressed in E. coli and tested for ribosome inactivating activity. A summary of several constructions and their properties is given below. Following the summary is a more detailed description of the experiments. Unless otherwise stated, all constructions are expressed in pGR1 derivatives (FIG. 8B) and numbering of nucleotides follows that in FIG. 7.

1. R34 (FIG. 7) represents the intact recombinant proRIP gene which encodes a protein of Mr value 34,000 and as expected is not a potent inhibitor of protein synthesis. Upon papain treatment it is processed into two associated polypeptides (approximately 16.5+11.5 kD by SDS Phastgel analysis) with very potent ribosome inactivating activity. N34 represents the native proRIP as isolated from nature.

2. R34-DL (DL=deleted linker) represents the proRIP without the linker. The sequences encoding 16.5K and 11.5K are joined directly without intervening linker DNA, i.e., nucleotides A-520 to A-594 are deleted (see FIG. 9). The R34-DL gene encodes a 30.6 kD protein which is a potent inhibitor of protein synthesis. Treatment of R34-DL with papain results in a 28 kD polypeptide with increased ribosome inactivating activity over the untreated molecule.

3. R30-DL encodes a polypeptide which contains neither the leader or linker regions of the proRIP, i.e., nucleotides G-40 to C-84 and A-520 to A-594 inclusive are deleted (see FIG. 10). It is also a potent inhibitor of protein synthesis. Upon papain treatment, R30-DL shows a slight decrease in molecular weight and a relatively small but significant increase in ribosome inactivating activity.

E. Expression of Insoluble Recombinant Maize proRIP (R34)

Expression of the recombinant maize proRIP in *E. coli* is accomplished by engineering the cDNA via PCR amplification. A 5' primer is synthesized which contains termination codons in all three reading frames to stop translation of vector-encoded proteins upstream of the maize proRIP cDNA. The primer also contains a Shine-Dalgarno sequence several base pairs upstream of an ATG start codon followed by 23 bases which are homologous to the maize proRIP cDNA. The 3' primer spans the 3' cDNA end-pUC19 junction (the primers are shown by the underlined regions in FIG. 7). PCR amplification of the cDNA in pUC19 using the GeneAmp kit (commercially available from Perkin Elmer-Cetus, Norwalk, Conn.) yields a predominant amplification product of approximately 1100 base pairs as expected.

Figure 8A:
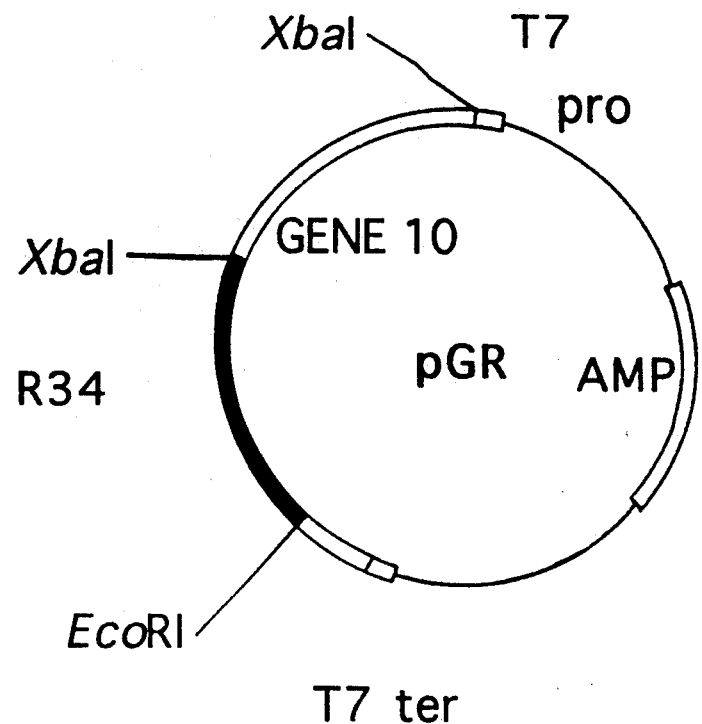
FIG. 8a illustrates the plasmid map of pGR.

The engineered, amplified product (FIG. 7), is purified from an agarose gel and ligated into the filled-in Hind III site of the expression vector pGEMEX-1 (commercially available from Promega Corp., Madison, Wis.) to give plasmid pGR (FIG. 8a). This is transformed into *E. coli* DH5c, (BRL), Gaithersburg, Md.). Plasmids containing the maize proRIP cDNA are isolated by colony hybridization (Sambrook et al., supra) with a 5' maize proRIP cDNA probe and characterized. Those containing the maize proRIP cDNA in the correct orientation are tested for expression. Plasmids are transformed into competent *E. coli* JM109(DE3) (Promega Corp., Madison, Wis.), transformed cells are grown in 15 ml cultures under ampicillin selection to an optical density at 600 nm of 0.4–1.0. Isopropylthio-$\beta$-galactoside (IPTG) is added to 1.3 mM to induce the production of recombinant RIP and the cultures are grown an additional 4 hours at 37° C. The cells are collected by centrifugation and stored as a pellet at −20° C.

The protein produced from the maize proRIP cDNA is analyzed by lysing the induced cells in TE containing 1 mg/ml lysozyme 37° C. for 15 min. The lysate is fractionated into a crude supernatant and pellet by microcentrifugation. The fractions are analyzed by SDS-PAGE using 20% Phastgels (commercially available from Pharmacia, Piscataway, N.J.). Coomassie blue staining and Western blot analysis of the gels with anti-maize RIP sera identify a 34 kD band which is greatly increased upon induction of the cells with IPTG. Cells not carrying the plasmid or containing the plasmid with the maize proRIP cDNA in the inverted orientation do not contain this 34 kD immuno-reactive band. The majority of the recombinant maize proRIP is contained in the cellular pellet suggesting the material is insoluble under these conditions.

To test if the recombinant proRIP (R34) could acquire the folding pattern of native proRIP (N34) the pellet fraction of an induced culture is dissolved in 6M guanidine HCl and allowed to denature at room temperature for 3 hours. The material is then diluted 200-fold into ice cold TE and incubated at 4° C. overnight to allow refolding of the denatured R34. The diluted material is then concentrated by a Centricon 10 device (commercially available from Amicon). To test whether refolded R34 could undergo the correct proteolytic processing to the fragmented form of the maize proRIP, the material is treated with 10 µg/ml papain for various times and samples are analyzed by SDS-Phastgel and Western blot analysis. The R34 material is processed to a stable mixture of two immuno-reactive bands which comigrate with N34 papain-processed material indicating the correct proteolytic processing had occurred.

Figure 8B:
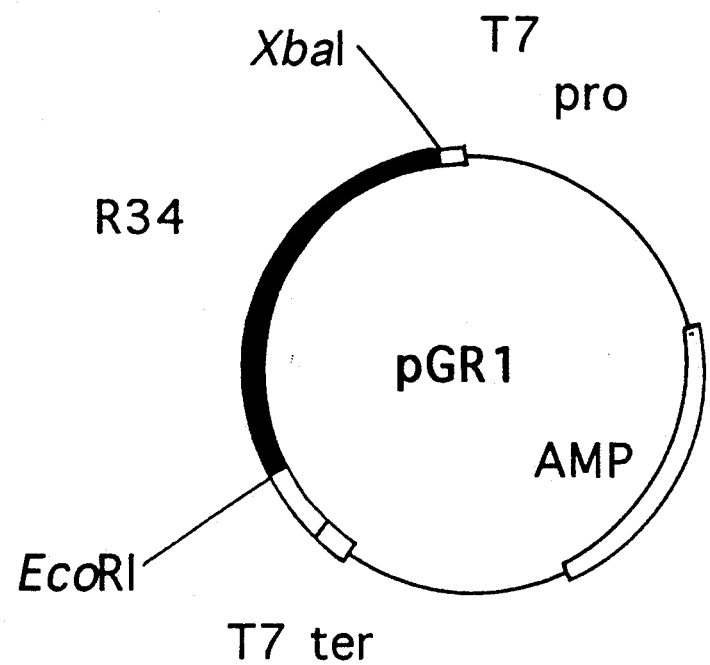
FIG. 8b illustrates the plasmid map of pGR1.

In an effort to simplify purification of the R34 polypeptide from induced lysates, the gene 10 coding region of the pGEMEX-1 vector is removed by cutting the maize proRIP gene-containing plasmid (pGR) with Xba I and gel purifying the vector/RIP DNA away from the gene 10 encoding DNA. Recircularization of pGR, now minus the gene 10 coding region, results in a plasmid called pGR1 (FIG. 8b).

The plasmid pGR1 is transformed into JM109(DE3) cells and tested for production of R34 following induction with IPTG. As with pGR, large amounts of R34 are identified in cellular lysates both by Western blot and Coomassie blue staining. Unlike pGR, R34 produced from pGR1 is soluble and fractionates in the supernatant of lysed cells. This soluble material is treated with papain at 10 µg/ml and the R34 produced from pGR1 is cleaved to products which comigrate with N34, papain-cleaved product. The papain-treated material inhibits translation of reticulocyte lysates at significantly higher dilutions than the untreated material, indicating that the soluble R34 is processed to an active form.

E. Expression of R34-DL

Confirmation that removal of the linker from maize proRIP activates the molecule is obtained independently through genetic engineering. The 75bp linker encoding region of R34 (A-520 to A-594 inclusive FIG. 7) is deleted using PCR amplification. The new construction R34-DL (DL =deleted linker) joins directly, in frame, the DNA encoding both the 16.5K and 11.5K fragments.

In the pGEMEX-1 system the R34-DL gene directs the synthesis of a polypeptide approximately 30.6 kD which is recognized by antisera specific for the maize RIP. At high dilution, *E. coli* lysates containing R34-DL protein are potent inhibitors of protein synthesis in rabbit reticulocyte lysates, in marked contrast to *E. coli* lysates containing the R34 polypeptide.

These genetic deletion data confirm that removal of the linker serves to activate the R34 (proRIP) molecule. This experiment also demonstrates that covalent linkage of the 16.5K and the 11.5K polypeptide fragments will still result in an active RIP. The maize RIP does not require a break in the polypeptide backbone for enzymatic activity, removal of the linker region is sufficient to confer potent ribosome inactivating activity.

In addition, when R34-DL lysates are treated with papain a slight decrease in the molecular weight of R34-DL protein is noted (from 30.6 to approximately 28kD). The R34-DL polypeptide remains intact, that is, it is not cleaved to the characteristic maize RIP 16.5K and 11.5K fragments. Associated with this small change in molecular weight is an increase in protein synthesis inhibition in the *E. coli* lysates. These data indicate that in bacterial lysates removal of the linker region activates the RIP 250-fold, but that additional processing from the ends of the protein increases the activity.

G. Expression of R30-DL

Another genetic construction is made using PCR technology to remove the leader region from R34-DL. The new construction called R30-DL (deleted for both the leader and linker) encodes a protein (approximately 29.5 kD) which is slightly smaller than R34-DL. *E. coli* lysates containing R30-DL appear to be even more potent inhibitors of protein synthesis than R34-DL lysates. Papain treatment of R30-DL containing lysates further enhances protein synthesis inhibiting activity. Following this treatment the R30-DL protein undergoes a slight decrease in molecular weight representing processing at the ends of the polypeptide. Therefore further enhancement of the ribosome inactivating activity of the RIP derivatives will occur on further genetic deletion of C- or N-terminal amino acids, and will eliminate the necessity for papain activation altogether.

Although the invention has been described in considerable detail, with reference to certain preferred embodiments thereof, it will be understood that variations and modifications can be affected within the spirit and scope of the invention as described above and as defined in the appended claims.

We claim:

1. A DNA isolate encoding a maize proRIP having a ribosome inactivating protein sequence and a linker sequence wherein the maize proRIP has the following amino acid sequence:

```
1   KRIVPKFTEI  FPVEDANYPY
        SAFIASVRKD  VIKHCTDHKG
41  IFQPVLPPEK  KVPELWFYTE
            LKTRTSSITL  AIRMDNLYLV
81  GFRTPGGVWW  EFGKDGDTHL
            LGDNPRWLGF  GGRYQDLIGN
121 KGLETVTMGR  AEMTRAVNDL
            AKKKKMATLE  EEEVKMQMQM
161 PEAADLAAAA  AADPQADTKS
            KLVKLVVMVC  EGLRFNTVSR
201 TVDAGFNSQH  GVTLTVTQGK
            QVQKWDRISK  AAFEWADHPT
241 AVIPDMQKLG  IKDKNEAARI
            VALVKNQTTA  AAATAASADN
281 DDDEA.
```

2. The DNA isolate of claim 1 designated R34.

3. A DNA isolate encoding a protein capable of substantially inactivating eukaryotic ribosomes, said protein having the following amino acid sequence:

```
MAEITLEPSD  LMAQTNKRIV  PKFTEIFPVE  DANYPYSAFI
ASVRKDVIKH  CTDHKGIFQP  VLPPEKKVPE  LWFYTELKTR
TSSITLAIRM  DNLYLVGFRT  PGGVWWEFGK  DGDTHLLGDN
PRWLGFGGRY  QDLIGNKGLE  TVTMGRAEMT  RAVNDLAKKK
KAADPQADTK  SKLVKLVVMV  CEGLRFNTVS  RTVDAGFNSQ
HGVTLTVTQG  KQVQKWDRIS  KAAFEWADHP  TAVIPDMQKL
GIKDKNEAAR  IVALVKNQTT  AAAATAASAD  NDDDEA.
```

4. The DNA isolate of claim 3 designated R34-DL.

5. A DNA isolate encoding a protein capable of substantially inactivating eukaryotic ribosomes, said protein having the following amino acid sequence:

```
MKRIVPKFTE  IFPVEDANYP  YSAFIASVRK  DVIKHCTDHK
GIFQPVLPPE  KKVPELWFYT  ELKTRTSSIT  LAIRMDNLYL
VGFRTPGGVW  WEFGKDGDTH  LLGDNPRWLG  FGGRYQDLIG
NKGLETVTMG  RAEMTRAVND  LAKKKKAADP  QADTKSKLVK
LVVMVCEGLR  FNTVSRTVDA  GFNSQHGVTL  TVTQGKQVQK
WDRISKAAFE  WADHPTAVIP  DMQKLGIKDK  NEAARIVALV
KNQTTAAAAT  AASADNDDDE  A.
```

6. The DNA isolate of claim 5 designated R30-DL.

7. A biologically functional expression vehicle containing a DNA isolate of claim 1, 3, 5, 2, 4 or 6.

8. A host cell transformed with the biologically functional expression vehicle of claim 7.

9. The transformed host cell of claim 8, wherein the host cell is a eukaryotic cell.

10. The host cell of claim 9, wherein the host cell is maize.

* * * * *